US007983465B2

(12) United States Patent
Leroux et al.

(10) Patent No.: US 7,983,465 B2
(45) Date of Patent: Jul. 19, 2011

(54) IMAGE RECONSTRUCTION METHODS BASED ON BLOCK CIRCULANT SYSTEM MATRICES

(75) Inventors: Jean-Daniel Leroux, Sherbrooke (CA); Rèjean Fontaine, Ascot (CA); Roger Lecomte, Sherbrooke (CA); Vitali Selivanov, Sherbrooke (CA)

(73) Assignee: Société De Commercialisation Des Produits De La Recherche Appliquée - Socpra Sciences Santé Et Humaines, S.E.C., Sherbrooke, Quebec (CA)

( * ) Notice: Subject to any disclaimer, the term of this patent is extended or adjusted under 35 U.S.C. 154(b) by 684 days.

(21) Appl. No.: 12/118,351

(22) Filed: May 9, 2008

(65) Prior Publication Data
US 2009/0123048 A1   May 14, 2009

Related U.S. Application Data

(60) Provisional application No. 60/924,311, filed on May 9, 2007.

(51) Int. Cl.
*G06K 9/00* (2006.01)
(52) U.S. Cl. .................. 382/131; 250/363.04; 378/4
(58) Field of Classification Search ................. 382/131
See application file for complete search history.

(56) References Cited

U.S. PATENT DOCUMENTS

| | | | | |
|---|---|---|---|---|
| 6,718,055 B1 * | 4/2004 | Suri | ............................... | 382/128 |
| 7,332,721 B2 * | 2/2008 | Worstell | .................... | 250/363.03 |
| 7,381,959 B2 * | 6/2008 | Manjeshwar et al. | ... | 250/363.03 |

(Continued)

FOREIGN PATENT DOCUMENTS
EP    0 670 067    7/1997

OTHER PUBLICATIONS

Baker et al., "Generalized approach to inverse problems in tomography: Image reconstruction for spatially variant systmes using natural pixels", Critical Review Biomedical Engineering, vol. 20, pp. 47-71 (1992).
Buonocore et al., "A natural pixel decomposition for two-dimensional image reconstruction", IEEE Trans. on Biomed. Eng., vol. 28, No. 2, Feb. 1981, pp. 69-78.

(Continued)

*Primary Examiner* — Jingge Wu
(74) *Attorney, Agent, or Firm* — Fay Kaplun & Marcin, LLP

(57) ABSTRACT

An iterative image reconstruction method used with an imaging system that generates projection data, the method comprises: collecting the projection data; choosing a polar or cylindrical image definition comprising a polar or cylindrical grid representation and a number of basis functions positioned according to the polar or cylindrical grid so that the number of basis functions at different radius positions of the polar or cylindrical image grid is a factor of a number of in-plane symmetries between lines of response along which the projection data are measured by the imaging system; obtaining a system probability matrix that relates each of the projection data to each basis function of the polar or cylindrical image definition; restructuring the system probability matrix into a block circulant matrix and converting the system probability matrix in the Fourier domain; storing the projection data into a measurement data vector; providing an initial polar or cylindrical image estimate; for each iteration; recalculating the polar or cylindrical image estimate according to an iterative solver based on forward and back projection operations with the system probability matrix in the Fourier domain; and converting the polar or cylindrical image estimate into a Cartesian image representation to thereby obtain a reconstructed image.

51 Claims, 14 Drawing Sheets

U.S. PATENT DOCUMENTS 7,557,352 B2 * 7/2009 Hefetz ................... 250/363.04
7,680,240 B2 * 3/2010 Manjeshwar et al. ............ 378/4

OTHER PUBLICATIONS

Hebert et al., "Fast MLE for SPECT using an intermediate polar representation and a stopping criterion", IEEE Trans. on Nucl. Sci., vol. 35, No. 1, Feb. 1988, pp. 615-619.

Hudson et al., "Accelerated image reconstruction using ordered subsets of projection data", IEEE Trans. on Med. Imaging, vol. 13, No. 4, 1994, pp. 100-107.

Kaufman, "Implementing and accelerating the EM algorithm for positron emission tomography", IEEE Trans. on Med. Imaging, vol. MI-6, No. 1, Mar. 1987, pp. 37-51.

Kearfott, "Comment: Practical Considerations", Journal of the American Statistical Associateion, vol. 80, No. 389, Mar. 1985, pp. 26-28.

Llacer, "Tomographic image reconstruction by eigenvector decomposition: Its limitations and areas of applicability", IEEE Transactions on Medical Imaging, vol. MI-1, No. 1, Jul. 1982, pp. 34-42.

Mora et al., "Polar pixels for high resolution small PET", Conf. Record 2006 IEEE NSS/MIC, San Diego, CA (2006), 6 sheets.

Selivanov et al., "Fast PET image reconstruction based on SVD decomposition of the system matrix", IEEE Trans. on Nucl. Sci., vol. 48, No. 3, Jun. 2001, pp. 761-767.

Shepp et al., "Maximum likelihood reconstruction for emission tomography", IEEE Trans. on Med. Imaging, vol. MI-1, No. 2, Oct. 1982, pp. 113-122.

Shim et al., "SVD pseudoinversion image reconstruction", IEEE Trans. on ASSP, vol. 29, No. 4, Aug. 1981, pp. 904-909.

Vandengerghe et al., Reconstruction of 2D PET data with Monte Carlo generated system matrix for generalized natural pixels, Physics in Medicine Biology, vol. 51, p. 3105-3125 (2006).

* cited by examiner

Fig. 14

IMAGE RECONSTRUCTION METHODS BASED ON BLOCK CIRCULANT SYSTEM MATRICES

PRIORITY CLAIM

This application claims the benefit of U.S. Provisional Patent Application Ser. No. 60/924,311 filed on May 9, 2007, the specification of which is expressly incorporated herein, in its entirety, by reference.

FIELD OF THE INVENTION

The present invention relates to the reconstruction of images, in particular but not exclusively tomographic images representing the distribution of some characteristic across a sectional plane (2D mode) or a volume (3D mode) of a body under investigation, from measurements of an apparatus.

The present invention relates more particularly, but not exclusively, to iterative reconstruction methods and to direct reconstruction methods based on the singular value decomposition (SVD) used for Positron Emission Tomography (PET) and for Single Photon Emission Computed Tomography (SPECT) and for Computed Tomography (CT).

BACKGROUND

Tomography refers to the cross-sectional imaging of an object from either transmission, emission or reflection data collected from many different directions. Tomographic imaging deals with reconstructing an image from such data, commonly called projections. From a purely mathematical standpoint, a projection at a given angle is the integral of the image in the direction specified by that angle. Most of the powerful new medical imaging modalities that have been introduced during the last four decades, such as Computed Tomography (CT), Single Photon Emission Computed Tomography (SPECT), Positron Emission Tomography (PET), Magnetic Resonance Imaging (MRI) and 3D ultrasound (US), were the result of the application of tomographic principles.

The present invention relates to general tomographic reconstruction problems and, therefore, can be adapted to address all the aforementioned imaging modalities. However, for convenience and simplicity, the present specification is concerned with resolving PET image reconstruction problems, keeping in mind that the present invention could be used to resolve general tomographic reconstruction problems.

Positron emission tomography is a non-invasive imaging modality which is said to be metabolic or functional since it allows to measure and localize the biodistribution of a radio-element injected inside the body under investigation. The fundamentals of PET imaging is based on the localization of a positron source within the tissues of the subject by the detection of two oppositely directed gamma rays, emitted during the annihilation of the positron. An approximate localization of the site of disintegration along a line is possible by detecting simultaneously the two annihilation photons with opposed detector of the camera. This region where the disintegration could have taken place, known as "line of response (LOR)", "tube of response (TOR)", or "coincidence line", is defined by the volume joining the two detectors that received the annihilation photons. The time of detection of both annihilation photons must be measured and compared to validate that the two photons where emitted at the same time and thus, have a high probability of coming from the same disintegration. A PET scan consists of measuring and comparing the time of occurrence of every detected photon in the camera to record the coincident events that occur between all possible detector pairs which represent all the TORs of the camera. Using those measurements, an image of the biodistribution of the tracer injected in the subject could be obtained with image reconstruction methods.

A PET imaging system is typically composed of many 511 keV gamma ray detectors disposed on at least one ring or on a stack of many rings of detectors. The system also include a signal processing unit used to extract information relevant to the PET measurements (e.g. the time, the energy and the position of the detected photon) and a coincident sorter unit used to verify and count coincident events between all pairs of detectors in the camera. The imaging system can be used in two-dimensional acquisition mode where coincidence measurements are performed only between detectors in the same ring. Some apparatus also allow three-dimensional acquisition mode where coincidence measurements can be performed between detectors at different ring positions.

The geometries and the disposition of all sensing elements in a system is an important aspect when addressing the problem of reconstructing an object from a measure of its projections. A first solution to this problem date back to the paper by Radon in 1917 which proposed the inverse-Radon transform. Those works lead to the development of analytical reconstruction algorithms which aim at solving the inverse-Radon transform by considering every tubes of response (TORs) of the camera as an infinite thin line joining the two coincident detectors. One of the most common algorithm of this class is the filtered backprojection (FBP) algorithm, which makes use of the projection-slice theorem. Some drawbacks of the method is the presence of artifacts and the misplacements of some radioactive objects in the reconstructed image due to the over-simplification of the TOR functions by an infinite thin line.

A solution to this problem consists of modeling more closely the function representing the detection sensibility along the TORs which depends on the geometries and on the position of the two coincident detectors. Such a function is commonly called a coincidence aperture function (CAF) and could be obtained analytically or from a Monte Carlo simulation. Using the CAF of every TOR of the camera, a probability matrix relating the radioactive density of every pixel in the image to the measurements made on every TOR of the camera could be obtained. The problem could then be represented by the following relation:

$$y = Af \qquad (1)$$

where each coefficient $a_{i,j}$ of the probability matrix A represents the probability that an event produced in the $j^{th}$ pixel of the image vector f has been detected by the $i^{th}$ detector pair of the measurement vector y. The resolution of this problem could be addressed by two broad class of image reconstruction methods: "direct methods" which consist of inverting the probability matrix to obtain the image directly from a vector-matrix multiplication between the inverted matrix and the camera measurements and "iterative methods" which consist of making some successive estimates of the density distribution of the image in respect to the probability matrix and to the measurements until the image converge to a solution that meet given criteria.

Direct and iterative methods both have some advantages and drawbacks. Irrespectively to the method used, the main goal of reconstructing an image from its projections is to obtained an image that is as close as possible to the true density distribution of the object being imaged. In that respect, characteristics like spatial resolution, image contrast, signal-to-noise (S/N) ratio are aspects which can improve the detection accuracy but these should not be obtained at the expense of having some artifacts in the image which could lead to false detections. The computation time of the algorithm can also play a role in the selection of the most appropriate algorithm to use for a given scanner and in a given context of utilization like in clinical applications. A review of prior methods will be made in the light of those considerations.

Direct Methods:

A direct image reconstruction method based on pseudo-inversion of matrices may be found in [Llacer, Tomographic image reconstruction by eigenvector decomposition: Its limitations and areas of application]. The idea was to multiply both side of equation 1 by the transpose of the probability matrix which result in:

$$A^T y = A^T A f \qquad (2)$$

and to obtain the image by inverting the matrix $A^T A$ which can be expressed as:

$$f = (A^T A)^{-1} A^T y \qquad (3)$$

The matrix to inverse is now $A^T A$ and the pseudo-inversion operation is facilitated by the fact that $A^T A$ is a symmetric matrix. In this form, the matrix $A^T A$ can be viewed as a two-dimensional blurring matrix of the PET imaging system since it is obtained from the product of a backprojector $A^T$ and a projector A of the imaging system. One of the drawback of the method is the high condition number (CN) (largest divided by smallest eigenvalue) of the blurring matrix for tomographic reconstruction problems. The high CN leads to imprecision in the computation of eigenvectors corresponding to the smallest eigenvalues. Another drawback is the computational burden of the pseudo-inversion operation. Moreover, the measurement must be backprojected by $A^T$ before being multiplied by the pseudo-inverse of $A^T A$ which, however, does not add much computation compared to the pseudo-inversion operation.

A method to accelerate the blurring matrix $A^T A$ pseudo-inversion was proposed by Barber [Barber, Image reconstruction, "European patent specification", 1992]. The method consists of taking advantage of the block circulant structure emanating from the blurring matrix $A^T A$ when the projector A and the backprojector $A^T$ are strip functions defined in the continuous domain. The pseudo-inversion of the block circulant blurring matrix can then be performed independently on smaller sub-matrices by using the properties of the Fourier transform. The discretization of the image into square pixel elements is performed during the last step of backprojecting the result of the multiplication between the inverted blurring matrix and the measurements which lead to the following relation:

$$f = A^T (AA^T)^{-1} y \qquad (4)$$

One can notice that equation 4 is equivalent to equation 3, but with a different operation ordering. Barber has also pointed out that the backprojector can be some other function than the transpose of the projector.

The coefficients of the block circulant $A^T A$ matrix can be viewed as a natural pixel decomposition of a two-dimensional image. Buonocore [Buonocore, A natural pixel decomposition for two-dimensional image reconstruction, 1980] was the first to propose the term "natural pixel" to define pixels arising naturally out of the geometry of the X-ray beam paths used to measure the projections. One advantage of such an image decomposition is that it preserved the symmetries between the TORs of a camera leading to a block circulant structure of the $A^T A$ matrix. The projector A and the backprojector $A^T$ used in this formulation of the problem are strip functions defined in the continuous domain. The discretization of the forward projection matrix A into square pixels in a Cartesian grid representation, like the projector used in [Llacer, Tomographic image reconstruction by eigenvector decomposition: Its limitations and areas of application], would broke the symmetries between the TOR functions and will therefore not lead to a block circulant blurring matrix. This observation was pointed out by Baker who also proposed using natural pixel to facilitate the inversion problem in tomographic image reconstruction [Baker, "Generalized approach to inverse problems in tomography: Image reconstruction for spatially variant systems using natural pixels", 1992]. In this work, Baker proposed to accelerate pseudo-inversion of the blurring matrix through the used of the singular value decomposition (SVD) on a Fourier transformed version of the block circulant blurring matrix. To obtain the final image, the result of the multiplication between the pseudo-inverse blurring matrix and the measurement vector is backprojected.

It was shown by Shim [Shim, "SVD Pseudoinversion image reconstruction, 1981] that the pseudo-inverse of matrices by singular value decomposition techniques can be performed directly on the system probability matrix A, as stated in equation 1. One advantage of performing the SVD directly on the system matrix A is that the CN for such problems will be lower then one obtained for the blurring matrix $A^T A$. When a lower CN is encountered, the SVD algorithm will be less affected by computer precision limitations which will lead to better estimate of smaller singular values and of the corresponding singular vectors. Another advantage of the method is that the reconstructed image can be obtained directly from the multiplication of the inverted matrix with the measurement vector which avoids the used of a backprojection matrix. In other words, the quality of the reconstructed image is not influenced by the modeling of the backprojection matrix. This is a significative improvement since it is easier and more precise to include all the physical aspects of the imaging process in the projection matrix than in the backprojection matrix. Vandenberghe [Vandenberghe, "Reconstruction of 2D PET data with Monte Carlo generated natural pixels] has shown that it is possible to include a more realistic modeling of the imaging process inside the natural pixels decomposition emanating from the blurring matrix $A^T A$ by using a Monte Carlo simulation. However, Vandenberghe fails to include the modeling of the system in the backprojection matrix.

A drawback of performing the SVD directly on the probability matrix A is the computational burden of decomposing such a large matrix for ill-posed problems. Selivanov [Selivanov, "Fast PET image reconstruction based on SVD decomposition of the system matrix] proposed to perform the SVD step only once for a given PET scanner configuration. The resulting image reconstruction algorithm is really fast since it required only a matrix-vector multiplication between the inverted probability matrix and the measurement vector. However, due to limitations in computation power, available memory size and floating point precision of current computer, the SVD inversion can only be performed for modest size imaging problem.

Iterative Methods:

Iterative image reconstruction methods consist of estimating the density distribution of the image in respect with the system probability matrix and the measurements made on all TORs of the imaging system. Two wide class of methods are based on this approach: Algebraic reconstruction methods and statistical reconstruction methods. Algebraic reconstruction methods consist of resolving directly the system of equation by some iterative process. Instead of solving directly the system of equations, statistical image reconstruction methods can include some probability distribution in the iterative process. Those methods thus have the advantage of taking into account the stochastic nature of the detection process. This could lead in a better estimate of the object density, especially in the case of low projection statistics.

It has been shown that iterative reconstruction methods, based on a probability matrix of the system, could lead to images with higher spatial resolution and with a more uniform signal-to-noise (SNR) distribution than analytical methods like FBP. Nevertheless, a drawback of iterative methods is the computational burden coming from the many iterations required before the image reach final convergence. Moreover, the number of computation required at each iteration step become more important as the size of the probability matrix A increased (equation 1). The size of the probability matrix depends on the number of TORs measured by the camera and on the number of pixels in the reconstructed image and also on the accuracy of the acquisition model use to derive the matrix. For an imaging system composed of many detector rings and operating in full three-dimensional (3D) acquisition mode, the events detected in millions of TORs can be recorded leading to a very huge system matrix and therefore required a lots of computations when 'true' 3D iterative image reconstruction is performed. By 'true' 3D iterative image reconstruction methods, we mean a method that use all relevant information collected by the camera to estimate every pixels of the image.

In contrast, some 'approximate' 3D iterative image reconstruction methods use data rebinning of 2D reconstructed image to estimate the 3D image distribution. In such algorithm, the 3D projection data is first sorts into smaller 2D data set containing the TOR measurements for each transaxial slice to be reconstructed. All the different slices are then reconstructed independently using a 2D iterative image reconstruction algorithm based on a smaller probability matrix which relates only the measurements and pixels belonging to the same 2D slice. All the 2D slices are then rebinned together to estimate the 3D image distribution. By decomposing the 3D image reconstruction problems into smaller independent 2D image reconstruction problems, a significant reduction of the computation time is achieved. The use of a smaller 2D probability matrix also avoids the cumbersome handling of a huge 3D probability matrix. Nevertheless, this oversimplification of the initial problems can lead to mispositioning and/or to non-optimal estimate of some source activity in the 3D image.

To accelerate 'true' 3D iterative image reconstruction methods and make them fast enough for day-to-day use in clinical applications, one can address one or more of the following problems: 1) the number of iterations required by the algorithm to converge, 2) the number of operations required in each iteration loop and 3) the size of the system matrix. The acceleration of 3D iterative methods can also be obtained by sharing the task of computation over many parallel processors and/or by using a more powerful computation unit.

In the literature, most effort in accelerating iterative image reconstruction methods have been concentrated in addressing the first aspect which consists of reducing the number of iterations required to converge to the optimal image. Probably the most known example of such an acceleration technique is the Ordered Subsets Expectation Minimization (OSEM) algorithm [Hudson, "Accelerated image reconstruction using ordered subsets of projection data", 1994] which leads to acceleration of the convergence of the well known Maximum Likelihood Expectation Minimization (MLEM) algorithm that was first proposed by Shepp and Vardi [Shepp, "Maximum likelihood reconstruction for emission tomography", 1982]. The OSEM algorithm consists in dividing the projection measurement into small subsets (or blocks) and updating the image estimate using only the data of one subset at a time. One complete iteration loop is completed when all the subsets have been used in the update of the image estimate. This strategy provides an order-of-magnitude acceleration over the MLEM algorithm which is proportional to the number of subsets used. Many other solutions to accelerate the convergence of iterative algorithms are proposed in the literature but will not be presented here since they have less to do with the present invention.

Another strategy for accelerating the speed of iterative algorithms consists of minimizing the number of operations involved in each iteration loop. For most iterative image reconstruction algorithms the main computational burden comes from the matrix-vector operations involved in the forward and back projection steps that are performed at each iteration loop. The number of operations in the forward and back projection steps depends on the size and on the sparsity of the system matrix. In PET, the matrix coefficients are non-null only for pixels (or voxels) which have a non-null probability of emitting a disintegration that is detected by a given TOR. Using a simplified geometrical model of the acquisition process, many matrix coefficients are null and do not have to be stored. By storing the system matrix in a sparse format, both the memory requirements and the computational burden are reduced by using only the non-null values while performing computations in the forward and back projection steps. However, for some complex 3D image reconstruction problems, the sparse probability matrix could still be very huge.

The size of the probability matrix is really becoming a problem when it is too large to fit in the random access memory (RAM) of a given processor or dedicated hardware computational unit. A solution consists in storing the precomputed system matrix in a larger memory location, usually a hard disk, and to access only sub-part of the precomputed system matrix during the forward and back projection steps. The overhead of reading large amount of information on a hard disk could lead to very long delay for the image reconstruction procedure. Another solution consists in recomputing on-the-flag all the system matrix coefficients at each iteration loop to avoid storing them. Some simplifications of the acquisition model should however be used while computing the system matrix coefficients to keep the computation time within acceptable delay. Those simplifications in the system matrix will affect the quality of the reconstructed image.

A strategy for reducing the memory requirements for storing the system matrix consists of taking advantage of the symmetries between the TORs of a camera to store only non-redundant part of the system matrix. In-plane symmetries come from the angular repetitions of blocks of detectors within the ring of an imaging system. In-plane angular symmetries can also be obtained by performing successive measurements taken at different angle position using for example a rotating detector gantry. For camera operating in 3D acquisition mode, one can also take advantage of the axial symmetries present between the different detector rings. Some mirror symmetries could also be retrieved for some camera configurations. Most image reconstruction methods presented in the literature are based on a Cartesian image representation which have the consequence of broking most of the system symmetries in the system matrix. A solution consists of using a basis function defined according to a polar or cylindrical coordinate grid that is specifically designed to preserve all symmetries of a given camera configuration in the system matrix. The idea of using a polar image was first proposed by Kearfott [Kearfott, K. J., "Comment: Practical considerations;", Journal of the American Statistical Association, March 1985, pp. 26-28]. This solution was proposed to overcome the memory limitation of computer of that time, according to the size of probability matrix used in two-dimensional iterative image reconstruction techniques. One drawback of the polar image configuration used by Kearfott is that a fixed number of pixels are used at every radius position which has the consequence of dividing the image into very thin pixels at the center and into wide pixels at the border of the field of view. The important size disparities between the innermost and the outermost pixels of the image could result in over resolution in the center of the image and in degradation of the imaging system spatial resolution farther from the center. Moreover, Kaufman argued that, for statistical reasons, pixels with similar area should be used by iterative algorithms.

To overcome the problem of size disparities between the polar pixels, Kaufman [Kaufman, Implementing and accelerating the EM algorithm for positron emission tomography] proposed to use a polar image with different number of pixels at each radius position and with variable distances between successive radius positions in such a manner that pixels of similar area are obtained. In this paper, Kaufman showed that important memory saving can be obtained by using a polar image in replacement of a Cartesian image. However, the proposed polar image reconstruction algorithm did not result in significant acceleration of the forward and back projection steps.

Hebert [Hebert, Fast MLE for SPECT using an intermediate polar representation and a stopping criterion] also proposed the use of a polar image representation. In this work, it was shown that the polar image based system matrix can be reordered into a matrix having a block circulant structure. The block circulant system matrix can then be converted in the Fourier domain in order to reduce the number of operations involved in the forward and back projection steps of iterative image reconstruction methods. One drawback of converting the probability matrix in the Fourier domain comes from the fact that a lot of null values in the matrix become non-null during the Fourier transform which increase the matrix size. Another drawback of the method proposed by Hebert, is that the polar image used has a constant number of pixels at every radius position which results in size disparities between innermost and outermost pixels. To avoid the potential problem of using pixels with size disparities in iterative algorithm, Hebert converts the polar image representation into a Cartesian image representation before performing the image update. However, this conversion from a polar to a Cartesian image representation and then from a Cartesian to a polar image representation can result in a loss of spatial resolution due to divergences between the pixels size and position of the polar and Cartesian images. Moreover, since a dense system matrix in the Fourier domain is used in the computation, the gain of speed compared to the traditional method based on a sparse system matrix in the spatial domain rapidly vanishes as the number of symmetries in the camera become small compared to the number of detectors within a ring.

OBJECTS OF THE INVENTION

An object of the present invention is to provide an imaging system and method to model the response functions of the apparatus which minimize the size of the system matrix that can be used by direct and/or by iterative image reconstruction methods.

Another object of the present invention is to provide fast methods for computing the pseudo-inverse of the said probability matrix using singular value decomposition and fast methods to compute the image using the pseudo-inverse matrix.

Another object of the present invention is to provide accelerated methods for computing the forward and back projection steps in the iteration loops of iterative image reconstruction methods.

SUMMARY

More specifically, in accordance with a first aspect of the present invention, there is provided an imaging system. The imaging system comprises: a plurality of detectors each so configured as to generate a signal which is used to make measurements of an object along a respective projection; a translating table so configured as to receive an object thereon and operable to translate in relation to the plurality of detectors; a signal processor so coupled to the plurality of detectors as to receive and process the signals generated by the detectors; the signal processor being so configured as to extract relevant information in accordance with an imaging modality of the imaging system; an acquisition system so coupled to the signal processor as to collect the information extracted by the signal processor and information about an actual position of the translating table; the acquisition system being so configured as to produce projection data; and an image reconstructor so coupled to the acquisition system as to receive the projection data and reconstruct an image in response to the projection data. The image reconstructor is so configured as to reconstruct the image by: choosing a polar or cylindrical image definition which comprises a polar or cylindrical grid representation and basis functions defined over the polar or cylindrical grid in order to preserve symmetries between lines of response of the imaging system; computing a probability matrix that relates each of the projection data to each basis function of the polar or cylindrical grid representation; restructuring the probability matrix into a block circulant matrix; computing a polar or cylindrial image of the object using the block circulant matrix in Fourier domain; and converting the computed polar or cylindrical image into a Cartesian image representation to thereby obtain a reconstructed image of the object.

According to a second aspect of the present invention, there is provided an iterative image reconstruction method to be used in connection with an imaging system that generates projection data. The reconstruction method comprises the steps of: (a) collecting the projection data generated by the imaging system; (b) choosing a polar or cylindrical image definition which comprises a polar or cylindrical grid representation and a number of basis functions positioned according to the polar or cylindrical grid so that the number of basis functions at different radius positions of the polar or cylindrical image grid is a factor of a number of in-plane symmetries between lines of response along which the projection data are measured by the imaging system; (c) obtaining a probability matrix that relates each of the projection data to each basis function of the polar or cylindrical image definition; (d) restructuring the probability matrix into a block circulant matrix and converting the probability matrix in Fourier domain to accelerate matrix-vector operations using the probability matrix; (e) storing and arranging in a suitable form the projection data into a measurement data vector; (f) providing an initial polar or cylindrical image estimate; (g) for each iteration; recalculating the polar or cylindrical image estimate according to an iterative solver that is based on forward and back projection operations with the probability matrix in the Fourier domain; and (h) converting the polar or cylindrical image estimate into a Cartesian image representation to thereby obtain a reconstructed image.

According to a third aspect of the present invention, there is provided an iterative image reconstruction method to be used in connection with an imaging system that generates projection data. The reconstruction method comprises the steps of: (a) collecting the projection data generated by the imaging system; (b) choosing a polar or cylindrical image definition which comprises a polar or cylindrical grid representation and a number of basis functions positioned according to the polar or cylindrical grid so that the number of basis functions at different radius positions of the polar or cylindrical image grid is a factor of a number of in-plane symmetries between lines of response along which the projection data are measured by the imaging system; (c) obtaining a probability matrix that relates each of the projection data to each basis function of the polar or cylindrical image definition; (d) restructuring the probability matrix into a block circulant matrix and converting the probability matrix in Fourier domain to accelerate matrix-vector operations using the probability matrix; (e) storing and arranging in a suitable form the projection data into a measurement data vector; (f) providing an initial polar or cylindrical image estimate; (g) for each iteration and using an iterative solver; (i) converting the polar or cylindrical image estimate in the Fourier domain so that it can be forward projected with the probability matrix in the Fourier domain to obtain a measurement data estimate that is further converted back in space domain using the inverse Fourier transform; (ii) computing a measurement correction vector using the measurement data estimate and the measurement data vector; (iii) converting the measurement correction vector in the Fourier domain so that it can be back projected with the probability matrix in the Fourier domain to obtain a polar or cylindrical image correction vector that is further converted back in the space domain using the inverse Fourier transform; and (iv) computing a new polar or cylindrical image estimate using a current polar or cylindrical image estimate and the polar or cylindrical image correction vector; going back to step (i) for further iterations until the polar or cylindrical image estimate reaches convergence; and (h) converting the polar or cylindrical image estimate into a Cartesian image representation to thereby obtain a reconstructed image.

According to a fourth aspect of the present invention, there is provided a direct image reconstruction method to be used in connection with an imaging system that generates projection data. The method comprises the steps of: (a) collecting the projection data generated by the imaging system; (b) choosing a polar or cylindrical image definition which comprises a polar or cylindrical grid representation and a number of basis functions positioned according to the polar or cylindrical grid so that the number of basis functions at different radius positions of the polar or cylindrical image grid is a factor of a number of in-plane symmetries between lines of response along which the projection data are measured by the imaging system; (c) computing a probability matrix that relates each of the projection data to each basis function of the polar or cylindrical grid representation; (d) restructuring the probability matrix into a block circulant matrix and converting the probability matrix in Fourier domain to accelerate matrix-vector operations when using the probability matrix; (e) storing and arranging in a suitable form the projection data into a measurement data vector; (f) pseudo-inverting the block circulant matrix using singular value decomposition (SVD) to produce a pseudo-inverse of the circulant matrix; (g) computing a polar or cylindrical image estimate by performing a matrix-vector product in the Fourier domain between the pseudo-inverse of the circulant matrix and the measurement data vector; and (k) converting the polar or cylindrical image estimate into a Cartesian image representation to thereby obtain a reconstructed image.

It is to be noted that the expression "lines of response" may be used interchangeably with the expression "tubes of response" herein and in the appended claims.

It is also to be noted that the expression "is a factor of" is to be construed as meaning "is equal, is an integer fraction or is an integer multiple of" herein an in the appended claims.

Furthermore, it should be noted that the terms "probability matrix" may be used interchangeably with the terms "system matrix".

The foregoing and other objects, advantages and features of the present invention will become more apparent upon reading of the following non restrictive description of an illustrative embodiment thereof, given by way of example only.

BRIEF DESCRIPTION OF THE DRAWINGS

In the appended drawings:

FIG. 14 is a double block circulant system matrix that can be obtained using a 3D imaging system with a similar configuration than the one presented in FIG. 12, but using this time a camera composed of two ring of detectors and a cylindrical image representation with 4 axial image slices;

DETAILED DESCRIPTION OF THE NON-RESTRICTIVE ILLUSTRATIVE EMBODIMENT

Figure 1:
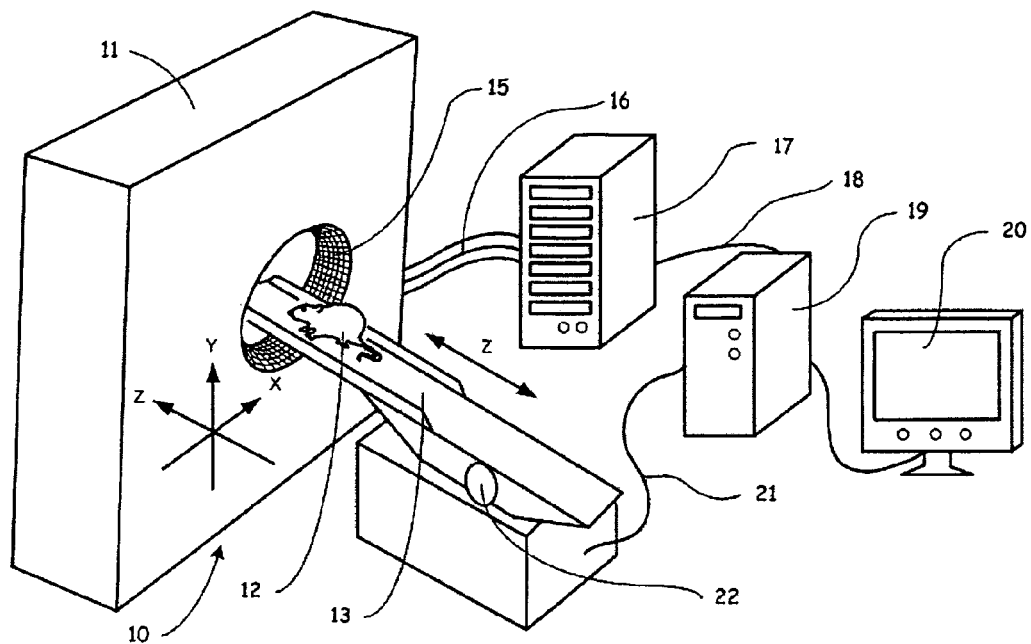
FIG. 1 is a pictorial view of a PET imaging system including a translating bed, an acquisition system, a main controller and image reconstructors utilizing methods of reconstructing an image of a subject.

Generally stated, a non-restrictive illustrative embodiment of the present invention provides for an imaging system and methods of computing image reconstructions using a system matrix that relates the measurements of the imaging system to the pixels (or voxels) of the image, wherein the pixels (or voxels) are positioned according to a polar or cylindrical coordinate grid. The imaging system can be measuring Positron Emission Tomography (PET) or can be other imaging modalities, for example, but not restricted to, Computed Tomography (CT), Single Photon Emission Computed Tomography (SPECT) and ultrasound imaging (US). The polar or cylindrical image is discretized according to basis functions defined over a polar coordinates image grid in such a way that the symmetries present between the tubes of responses (TORs) of the imaging system are preserved during the computation of the system matrix coefficients. Those symmetries allow to reorder the system matrix into a block circulant matrix. The non-restrictive illustrative embodiment of the present invention also provides ultra-fast image reconstruction methods based on the multiplication of a pseudo-inverse of the block circulant probability matrix with the camera measurements in the Fourier domain. The non-restrictive illustrative embodiment of the present invention also provides methods for accelerating iterative image reconstruction algorithms by performing the forward and backward matrix multiplication operations with block circulant matrices in the Fourier domain.

More specifically, the imaging system includes detecting elements positioned in such a way that many symmetries arise from the lines of response of the imaging system which can be used to reduce the size of the system probability matrix and to accelerate the image reconstruction methods. The imaging system also includes a translating table or a bed which can be translated axially (z-axis) and a system that can monitor the bed position and save this information in the data flow. For three-dimensional image reconstruction, the bed axial position can be used to add more axial symmetries in the imaging system and to increase the measurement statistics by combining the information coming from the acquisition frame performed at different bed positions.

An image discretized according to a polar or cylindrical coordinates grid is used to create a system probability matrix which has redundancies between the matrix coefficients related to the symmetric TORs of the imaging system. This allows to re-use some parts of the system matrix for all the symmetric TORs. By storing only non-redundant parts of the system matrix, the memory requirement is reduced by a factor equal to the number of system symmetries. The probability matrix coefficients can be derived from analytical models, Monte Carlo simulations or by some other methods. The polar or cylindrical image is designed in such a way that the symmetries between the TORs of the camera are preserved during the computation of the probability matrix coefficients. This condition is satisfied given that the number of pixels (or voxels) at every radius position of the polar or cylindrical image is a factor of the number of in-plane symmetries, such as is equal or is an integer fraction or an integer multiple of the number of in-plane symmetries. The pixels used in the polar or cylindrical image can be overlapping and/or can be of different shape, as long as the computation of the coefficients of the matrix preserves the redundancies in the system probability matrix.

It is well known that the product operation between a circulant matrix and a vector results in less operations when performed in the Fourier domain. This property between circulant matrix and the Fourier transform can also be exploited for block circulant matrices. In the case of two-dimensional image reconstruction problems, the system matrix have a block circulant structure and can be converted in the Fourier domain by using Fourier transform, or Fast Fourier Transform (FFT), applied on the first column of every small circulant sub-matrices. The same technique also applies to three-dimensional (3D) image reconstruction problems. However, the presence of axial symmetries in 3D problems can also be used in such a way that the system matrix can be reordered into a block circulant structure where each block includes block circulant matrices. In one example, the three-dimensional probability matrix can be converted in the Fourier domain only once, which results in performing the Fourier transform only on small circulant sub-matrices made from in-plane system symmetries. In another example, the three-dimensional probability matrix can be converted in the Fourier domain twice, which results in first performing the Fourier transform on circulant sub-matrices made from in-plane symmetries and then performing a second Fourier transform on circulant sub-matrices made from axial symmetries.

Furthermore, ultra-fast image reconstruction methods based on the multiplication of a pseudo-inverse of the block circulant system matrix with the camera measurements in the Fourier domain are provided. The matrix pseudo-inverse is obtained using singular value decomposition (SVD) techniques. The block circulant system matrix can be obtained from two-dimensional or three-dimensional image reconstruction problems. The non-restrictive illustrative embodiment of the present invention comprises the preliminary steps of computing the system probability matrix for the selected imaging system and polar or cylindrical image representation, reordering the system matrix into a matrix having a block circulant structure and converting the block circulant matrix in the Fourier domain. The image reconstruction methods comprise the steps of: 1) performing the SVD decomposition on the block circulant system matrix in the Fourier domain, 2) using the SVD result to compute the pseudo-inverse of the system matrix, 3) performing the matrix-vector multiplication between the pseudo-inverse matrix and the measurement vector in the Fourier domain to obtain the image vector and 4) performing the inverse Fourier transform on the image vector and 5) performing a polar-to-Cartesian transformation on the image vector to obtain an image that can be visualized on a conventional display. Different variations in every step of this procedure are possible leading to different algorithms having some advantages and some inconveniences. A first image reconstruction algorithm consists in performing step 1 to step 5 each time a new measurement data set is to be reconstructed. This method is slow but also gives the maximum flexibility since the system matrix can be modified prior to the reconstruction procedure. A second image reconstruction algorithm consists in performing step 1 only once and performing step 2 to step 5 each time a new measurement data set is to be reconstructed. This method allows to modify the regularization parameter in step 2 to control the trade-off between the spatial resolution and the noise amplification in the reconstructed image. A third image reconstruction algorithm consists in performing step 1 and step 2 once and performing step 3 to step 5 each time a new measurement data set is to be reconstructed. This method allows to update the image in a continuous fashion by reconstructing independently small groups of pixels (or voxels).

Also, methods for accelerating iterative image reconstruction techniques by performing the forward and back projection matrix-vector multiplication operations with a block circulant matrix in the Fourier domain are provided. The block circulant matrix can be obtained from two-dimensional or three-dimensional image reconstruction problems. The iterative algorithm can be a version of the Maximum Likelihood Expectation Minimization (MLEM) or a version of another algorithm, like for example, but not restricted to, Ordered Subset Expectation Minimization (OSEM), Rescaled Block Iterative (RBI), Block Iterative Simultaneous MART algorithm (BI-SMART) or Penalized Weighted Least-Squares (PWLS) algorithm.

Irrespectively to the iterative algorithm used, the non-restrictive illustrative embodiment of the present invention comprises the preliminary steps of computing the system probability matrix for the imaging system and the polar or cylindrical image representation, reordering the system matrix into a matrix having a block circulant structure, converting the block circulant matrix in the Fourier domain and saving the resulting Fourier matrix in a sparse matrix format. An advantage of the non-restrictive illustrative embodiment of the present invention comes from the saving of the complex system matrix into a sparse matrix format which allows to access only a group of non-null data when matrix-vector operations are performed.

Irrespectively to the iterative algorithm used, the non-restrictive illustrative embodiment of the present invention comprises the steps of 0) providing a first image estimate, 1) converting the image estimate in the Fourier domain, 2) multiply completely or partly the image estimate with the direct system matrix in the Fourier domain to obtain an estimate of all or part of the apparatus measurements in the Fourier domain, 3) convert the measurements estimate back in the time domain to apply a correction with the measurements acquired by the imaging system, 4) transform the obtained measurement correction vector in the Fourier domain, 5) multiply completely or partly the measurement correction vector with the transposed system matrix in the Fourier domain to obtain all or part of the image correction vector in the Fourier domain, 6) convert the image correction vector back in the space domain to apply the correction to the current image estimate and 7) go back to step 1 until convergence is achieved. When the iteration loop is stopped, the non-restrictive illustrative embodiment of the present invention comprises one last step of converting the polar or cylindrical image into a square pixel Cartesian image so that the image can be shown on a conventional display. There are provided different methods for implementing the aforementioned steps of the iterative algorithm so that the time required to perform all operations included in one iteration loop is minimized for the image reconstruction problem and for the processor or hardware architecture used. In one embodiment, the conversion of the sparse block circulant system matrix in the Fourier domain can be performed on-the-flag during the iteration loop to minimize the memory requirements for storing the system matrix. Memory requirements can be reduced even more by computing on-the-flag the system matrix coefficients at each iteration loop.

While the non-restrictive illustrative embodiment of the present invention is described with respect to apparatus and methods of reconstructing an image using techniques for positron emission tomography (PET) imaging systems, the following apparatus and methods are capable of being adapted for various purposes including, but not limited to the following applications: Computed Tomography (CT) systems, X-ray imaging systems, Single Photon Emission Computed Tomography (SPECT) systems, ultrasound systems and other applications known in the art.

Referring to FIG. 1, a pictorial view of a PET imaging system 10, utilizing methods of reconstructing an image of a subject 12 is shown. A high spatial resolution PET Imaging system 10, dedicated for small animal 12, is illustrated as an example only, the non-restrictive illustrative embodiment of the present invention can also be applied to cameras dedicated to human subjects which can have a lower spatial resolution. The imaging system 10 includes a gantry 11 which contains one or many detector rings 15. Each detector 15 emits a signal when it detects one of the two annihilation photons generated by a beta disintegration coming from tracers injected inside the subject 12. The gantry 11 also includes electronic and/or digital circuits which amplify and process the signal produced by the detectors 15 in order to extract valuable information for the PET measurement. PET information is transmitted from the gantry 11 to a mass storage unit 17 through high speed communication links 16. The imaging system 10 also includes an operator console 19 which is used to send instructions to the main controller (33, FIG. 2) by some links 21 to control the PET acquisition processes and the bed 13 position. The bed 13 position can be translated along the z-axis direction inside the rings of detector 15 by sending commands to a high precision step motor 22. The operator console can also retrieve valuable PET information from the mass storage unit 17 through some links 18 and process the data to reconstruct an image of the density distribution of the tracer injected in the subject 15. The image can be sent to a display 20 for visualization.

Figure 2:
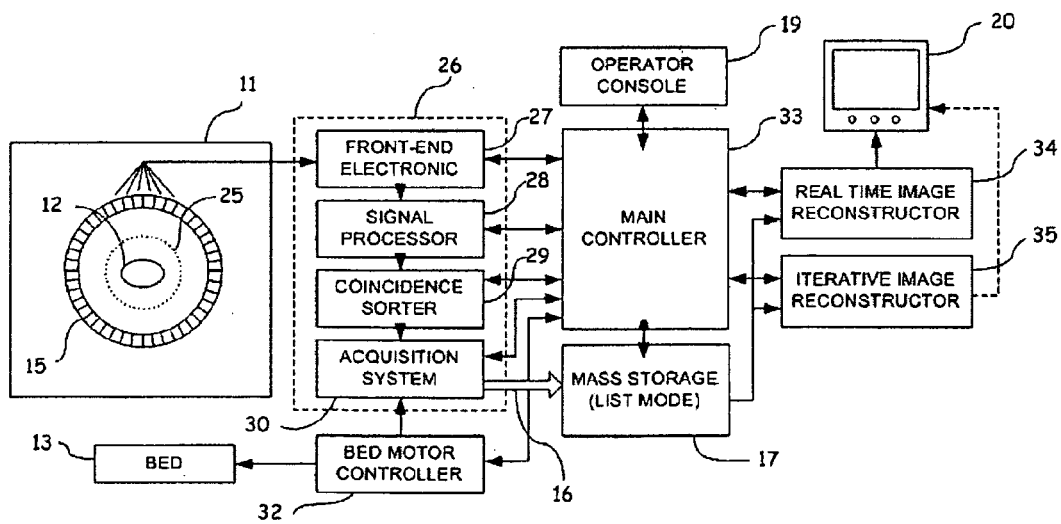
FIG. 2 is a block diagrammatic view of the main acquisition process of the imaging system including a translating bed, a signal processing chain, an acquisition system, a main controller, a mass storage unit and image reconstructors utilizing methods of reconstructing an image of a subject.

A more detailed description of the acquisition process is illustrated in a block diagrammatic view of the imaging system 10 in FIG. 2. The acquisition process is controlled from an operator console 19 which is used to send commands to the main controller 33. The main controller 33 can control the detectors 15, the front-end electronics 27, the signal processor 28, the coincidence sorter system 29, the acquisition system 30 and/or the bed motor controller 32. The front-end electronics 27 are used to amplify and shape the signal coming from all the detectors within the rings 15. As soon as a photon is detected by a detector 15, valuable PET information, like for example, but not limited to, the time stamp, the detector address and the signal energy are extracted by signal processors 28. Signal processors 28 can be composed of analog and/or digital circuits. All events detected by the signal processor 28 are sent with all their information to the coincidence sorter system 29 in order to retrieve the pair of photons that have been detected in a time nearby, thus having a high probability of coming from the same disintegration. Valid coincidence events, the ones that contribute to the count of a given tube of response (TOR) of the camera, are sent to a mass storage unit through fast communication links 16 to be saved. The flow of information being sent by the acquisition system 30 to the mass storage unit 17 includes information about the axial (z-axis) bed 13 position. This information is sent by the bed motor controller 32. An accurate axial positioning of the bed 13 is a useful information according to some aspects of the present invention and, therefore, this information can be included by some means in the acquisition data flow. During the acquisition process, the operator can ask for a real time image reconstruction of the subject 12 through a command send from the operator console 19 to the main controller 33. Coincidence measurements are then retrieved from the mass storage unit 17 and sent to the real-time image reconstructor 34 that reconstructs a two-dimensional or a three-dimensional image of the subject in a very short time. The image is sent to a display unit 20 and is continuously updated with new collected data as the acquisition progress. The reconstructed image will represent the density distribution of the tracer injected in the subject 15 inside the region include in the camera useful field of view (FOV) 25. During or after the acquisition process, the operator can ask for an iterative image reconstruction through a command sent from the operator console 19 to the main controller 33. The coincidence measurements are then sent to the iterative image reconstructor 35 for a two-dimensional or a three-dimensional image reconstruction. The iterative image reconstructor 35 is slower than the real time image reconstructor 34 but can lead to images of better quality. Although the real time image reconstructor 34 and/or the iterative image reconstructor 35 are methods that can be performed by a conventional PC, a more powerful computer or dedicated hardware computation unit can also be used to accelerate the image reconstruction at a higher cost.

An aspect of the non-restrictive illustrative embodiment of the present invention is to provide a fast two-dimensional and/or three-dimensional image reconstructor 34 which allows for the instant visualization of the image estimate while the patient is being scanned. This would make early identification of problems related to data acquisition easier. For example, subject 12 positioning would be facilitated, thus preventing tracer reinjection and retaking scans if the desired region-of-interest (ROI) is found to be (partially) outside the FOV. Having an image online, one would also be able to stop scanning as soon as the data statistics is deemed sufficient which would allow to increase the patient throughput.

The fast image reconstructor 34 can also be used to perform fast visual inspection of many 2D or 3D acquisition data frames, previously saved into the mass storage unit 17 or into some other storage unit, in order to retrieved data sets which contain the most valuable information for answering a given question. A slower but, by some means, more accurate iterative image reconstructor 35 can then be used to reconstruct the selected data set to provide an image of higher quality for the final diagnostic. In that respect, it is very advantageous to use the image reconstructor for reconstructing the many acquisition frames obtained from gated and/or dynamic acquisitions.

The real time image reconstructor 34 forms a direct method based on the multiplication, in the Fourier domain, of an inverted block circulant system matrix with a vector containing the measurement collected by an imaging system. The inverted block circulant matrix is obtained by the pseudo-inversion of a block circulant probability matrix with singular value decomposition (SVD). The accelerated iterative image reconstructor 35 solves, by the use of different kind of iterative solvers, an equation relating a vector containing the imaging system measurements to a vector containing the pixels (or voxels) value of an image through a block circulant probability matrix. The iterative methods are accelerated through the use of a block circulant system matrix in the Fourier domain for performing the forward and the back projection steps which are required by most iterative image reconstruction solvers. By considering, for example, that the real time image reconstructor 34 and the iterative image reconstructor 35 are optimized to reconstruct images for the same imaging system 10, both reconstructors will be based on the same block circulant system probability matrix. To avoid redundancies, the following description will be separated into three main sections. The first section will present the different aspects relating to the conception of the block circulant system probability matrix. The second section will present the different aspects relating to the real time image reconstructor 34 based on the SVD pseudo-inversion of the block circulant system matrix. The third section will present the different aspects relating to the iterative image reconstructor 35 based on different solvers which use the block circulant system matrix to accelerate computation in the forward and back projection steps in the iterative loop.

Conception of the Block Circulant Probability Matrix

Tomographic imaging involves a limited number of measurements of some physical property of interest taken along projections of an object having a continuous spatial distribution. The process of measuring data along projections is naturally represented by a discrete-continuous model that relates the discrete measurements to some integral transformation of a function of continuous spatial variables. This could be stated by the following relation:

$$\bar{y}_i = \iiint_{\Omega} f(x,y,z) h_i(x,y,z) dx dy dz, \quad i=1,\ldots,N \quad (5)$$

where $\bar{y}_i$ is one of the N discrete measurements, f(x, y, z) is the spatial distribution of the object at (x, y, z) and $h_i$(x, y, z) represent the contribution of the $i^{th}$ measurement of a point of unit strength located at (x, y, z). The parameter Ω denotes the finite domain of the spatial distribution where the integration in the continuous domain is performed. For example, in emission tomography, the limit Ω is due to the fact that the contribution of the image to a measurement $\bar{y}_i$ taken along a given tube of response (TOR) of the apparatus are null or could be neglected for region of the image falling outside the TOR.

In order to solve tomographic image reconstruction problems with the methods of the present invention, the discrete-continuous model of equation 5 is converted into a discrete-discrete model. The conversion of the continuous image representation into a discrete image representation can be performed by using a finite series expansion involving a chosen set of basis functions. The obtained discrete image representation $\bar{f}$(x, y, z) is now an approximation of the continuous image representation f(x, y, z) generated by the linear combination of a finite number B of basis functions:

$$\bar{f}(x, y, z) = \sum_{j=1}^{B} \bar{f}_j b_j(x, y, z) \quad (6)$$

where we denote the $j^{th}$ basis function by $b_j$(x, y, z) and we denote by $\bar{f}_j$ the coefficient that multiplies this basis function. More concretely, the role of the basis function is to subdivide the continuous image into small finite size area or volume, called pixels or voxels, where the weight (or value) of each individual pixel is set by the coefficient $\bar{f}_j$. Using the new discrete image representation, the process of measuring data along projections that was stated in equation 5 can be replaced by the following relation:

$$\bar{y}_i = \sum_{j=1}^{B} a_{i,j} \bar{f}_j \quad (7)$$

where $a_{ij}$ is the contribution of the $j^{th}$ basis function to the $i^{th}$ measurement. When stated in matrix-vector format, the problem of reconstructing an image from its projections can be described by:

$$\bar{y} = A\bar{f} \quad (8)$$

where $\bar{y}$ is a vector of N projection data, A is the N×B system matrix and $\bar{f}$ is a vector representing the source activity distribution in B source voxels. Using for example positron emission tomography (PET), each coefficient $a_{i,j}$ of the system probability matrix A can represent the probability that an event produced in the $j^{th}$ voxel of the image vector $\bar{f}$ been detected by the $i^{th}$ detector pair of the measurement vector $\bar{y}$. Using as another example, but not limited to, X-ray computed tomography (CT), each coefficient $a_{i,j}$ of the probability matrix A can represent the probability that an X-ray photon travelling through the $j^{th}$ voxel of the image vector $\bar{f}$ will be absorbed for the $i^{th}$ line of response (LOR) of the measurement vector $\bar{y}$, the LOR being formed by the current position of the X-ray source and the impinging detector.

According to equation 8 and equation 6, the system matrix A depends both on the nature of the apparatus leading to the measurement vector $\bar{y}$ and on the basis function $b_j$(x, y, z) used to discretized the image into a vector $\bar{f}$ of B source voxels. The imaging system will in turn depends on the physics relating to the imaging modality, on the geometry and position of the detecting elements of the apparatus, in some cases on the characteristics of an external source and on other considerations specific to the given imaging modality used.

Irrespectively to the imaging modality used, a two-dimensional (2D) and/or a three-dimensional (3D) system probability matrix A with a block circulant structure is provided in order to reduce the number of different coefficients $a_{i,j}$ that are computed and/or that are stored in memory to fully defined the system matrix A. Moreover, the properties of the Fourier transform are used to reduce and/or to accelerate the matrix-vector operations between the block circulant system matrix A and the image vector $\bar{f}$ and/or the measurement vector $\bar{y}$. The block circulant system matrix can be obtained by taking advantage of the symmetries arising between the tube of responses (TORs) of a given imaging system through the use of a 2D or a 3D image with basis functions positioned according to a polar or cylindrical coordinate grid. As an example, the block circulant system matrix A will be determined for the case of positron emission tomography. The method for obtaining the probability matrix can be adapted to other imaging modalities.

In the non-restrictive illustrative embodiment of the present invention, the geometry and the positioning of the detecting elements inside the rings of the imaging system should be designed in order to maximize the number of symmetries arising between the TORs of the camera. Some other considerations related to the design of the apparatus, like for example, but not limited to, the use of a translating bed for which the axial (z-axis) position can be retrieved and inserted into the flow of data, can allow to add more symmetries in the system. The maximization of the number of symmetries in the apparatus will in turn provide a maximal reduction of the size of the system matrix and a maximal acceleration of the computational speed for methods related to the image reconstruction using the projection data and the system matrix.

Figure 3:
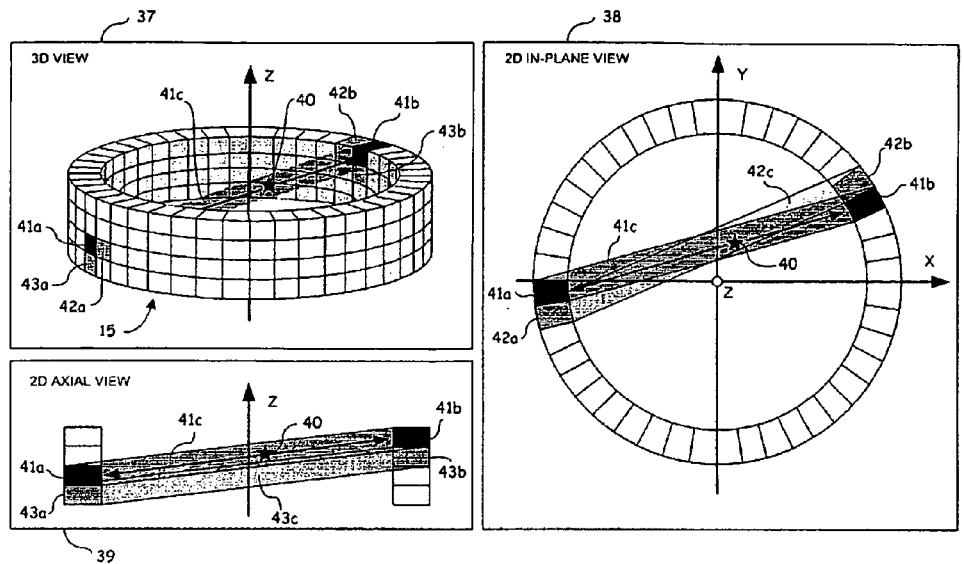
FIG. 3 is a pictorial view of all available symmetries between the TORs of an imaging system with perfect in-plane and axial symmetries between all the detecting elements.

A pictorial view of the detector rings 15 of an imaging system with perfect in-plane and axial symmetries between all the detecting elements is shown in FIG. 3. By the term perfect in-plane symmetries it is inferred that any detector position within the ring could be obtained by a rotation relative to the ring center of an other detector from an angle equal to $2\pi k/D$ where D is the number of detectors in the ring and k is an integer from 1 to D. By the term perfect axial symmetries it is inferred that a translation parallel to the axial direction (z-axis) from a given distance d or −d should lead to a perfect geometric match between all the detectors of two succeeding rings and this must be true for all the rings in the apparatus.

An example of a PET event detected within the detector rings 15 is shown in FIG. 3 in a 3D view 37, a 2D in-plane view 38 and a 2D axial view 39. A positron disintegration 40 emits two annihilation photons in opposite directions along a line falling inside the TOR 41c formed by the detectors 41a and 41b of the camera. The probability of detecting a PET event 40 occurring somewhere inside the TOR 41c formed by the volume in between the coincident detectors 41a and 41b will depend on their relative position and orientation from each other and on the position of their respective neighbor detectors. The position of the neighbor detectors, for example, the detector 41b having the neighbors 42b and 43b, can have an impact on the probability of detecting an impinging photon at a given incidence angle since the photon could have traveled in a neighbor detector (42b and 43b) before entering in the detector (41b).

Referring to the 2D in-plane view 38 of FIG. 3, it is shown that the TOR 42c formed by the coincident detectors 42a and 42b will have the same response function than the TOR 41c formed by the coincident detectors 41a and 41b because of the system in-plane symmetries. For a camera with perfect in-plane symmetries, the total number of in-plane rotation symmetries will be equal to the number of detectors within the ring. In this particular case, a different response function will only be required for TORs passing at different distances (bin position) from the center 44 of the ring. Here, the term "bin position" is used to define TORs passing at different distance from the center 44 of the ring. Accordingly, the number of TORs having a different response function will be reduced by a factor equal to the number of in-plane symmetries for TORs not passing through the ring center (all bins except the first one) and by a factor equal to half the number of in-plane symmetries for the TORs passing exactly through the ring center (first bin position).

Figure 4:
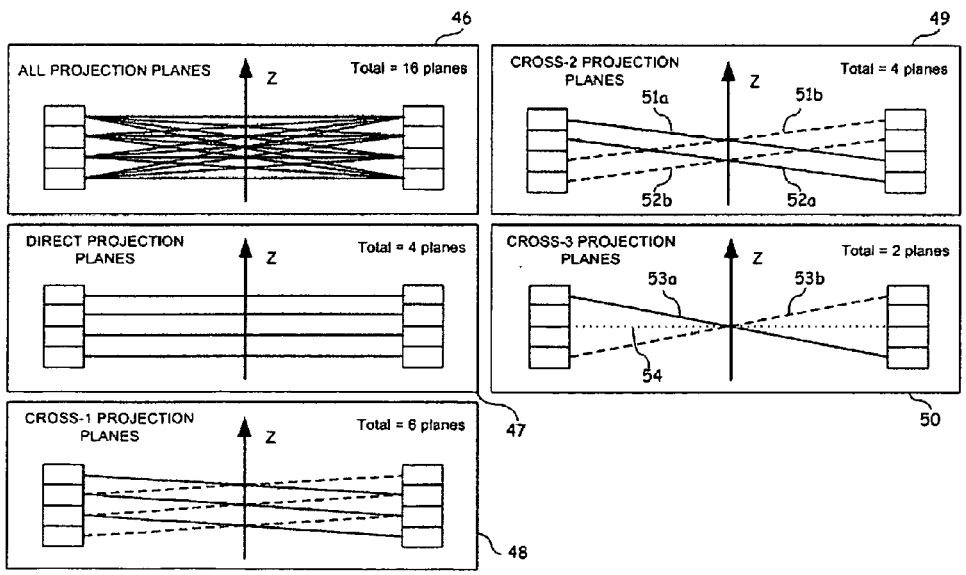
FIG. 4 is an illustration of all possible projection planes for a 4-ring scanner architecture.

Referring now to the 2D axial view 39 in FIG. 3, it is shown that the TOR 43c formed by the coincident detectors 43a and 43b will have the same response function than the TOR 41c formed by the coincident detectors 41a and 41b because of axial translation symmetries. For a scanner with perfect axial symmetries, the maximum number of axial translation symmetries is equal to the number of detector rings. However, for TORs formed by coincident detectors in different rings, the number of parallel TORs currently measured by the apparatus will be less than the number of rings. This statement is illustrated in FIG. 4 where all possible projection planes for a 4-ring scanner architecture are drawn. For direct projection planes 47, which are TORs formed by detectors at the same ring position, the number of measured TOR planes is equal to the number of rings in the apparatus. However, for projection planes formed by detectors at different ring positions, denoted here by the term cross-X projection planes where X represents the ring position difference between the coincident detectors, the number of parallel projections will depends on X. One should also notice the presence of a mirror symmetry between two projection planes at each parallel position. A mirror symmetry between two cross-3 projection planes (TORs 53a and 53b) is illustrated in FIG. 4. The mirror symmetries according to a reflection plane (54) can be exploited to allow reusing of one TOR response function for the mirrored TORs (53a and 53b). Accordingly, for an apparatus with perfect axial symmetries, the parallel and the mirrored axial symmetries allow to fully define the system probability matrix by using only one TOR function for the direct projection planes 47 and one additional TOR function for every cross-X projection planes (48, 49, 50). This will lead to a reduction of the memory requirement by a factor equal to the number of rings.

Figure 5:
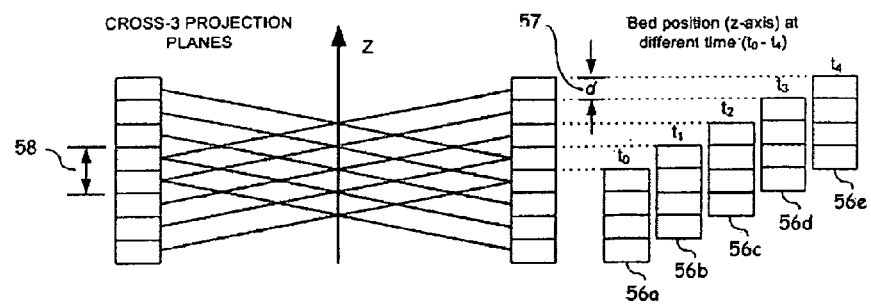
FIG. 5 is an illustration of a technique for merging the information of the cross-3 projection planes taken at different bed positions to improve the statistics collected on each projection plane for a 4-ring scanner with perfect axial symmetries.

In the non restrictive illustrative embodiment of the present invention, the number of axial symmetries of an apparatus can be extended to a number higher than the number of detector rings by the use of bed translations in the axial direction. The method required that information about the bed position could be retrieved and included in the data flow during the acquisition process as illustrated in FIG. 2. The method consists of translating the bed position along the axial direction (z-axis) by a distance that is equal to an integer factor of the distance d separating two symmetric projection planes. Since some of the TOR measurements acquired by the apparatus at different bed positions can partly recover the same scan region, it could be advantageous to combine the measurements taken at different bed positions to improve the statistic collected on each projection plane. This strategy is illustrated in FIG. 5 for a 4-ring camera with perfect axial symmetries between the rings. For reason of visibility, only the TORs of the cross-3 projection planes (50 in FIG. 4) are illustrated. Nevertheless, the method also applies for other projection planes. By moving the bed position by a distance d 57 equal to the distance between two symmetric projection planes, the data set (or frames) acquired at different bed positions (56a-56e) can be recombined and summed together to form an extended data set. One should notice that for the direct, cross-1 and cross-2 projections planes, some TORs coming from two or more acquisition frames taken at different bed positions will be taking measurements of exactly the same region. For example, considering that FIG. 4 and FIG. 5 both refer to the same 4-ring apparatus, the TORs of the cross-2 projection planes 51b and 51a measured at the bed position 56a will respectively be measuring the same scan region than the TORs of the cross-2 projection planes 52b and 52a taken at the bed position 56b. This reasoning can be extended to all bed positions taken during the whole acquisition process and to all the different projection planes. For the example in FIG. 5, this will lead respectively to four, three and two times more statistics collected on direct, cross-1 and cross-2 projection planes. Since there is only one cross-3 projection plane measured by a 4-ring scanner, those projections will never overlap during bed translations except if the displacement is less than a detector height. This overlap of information, which will be more or less important on certain projection planes, should be considered during the normalization of the system probability matrix so that the true acquisition process is modeled correctly. Another solution would be to rescale directly the projection data.

One advantage of recombining measurements taken at different bed positions into one extended data set that can be inputted to the image reconstruction procedure is that the maximum information, and thus the maximum statistics, could be used to reconstruct every region of an object being scanned. Ultimately some region 58 of the object will be crossed by all possible projection planes. One could also improve the axial spatial resolution of the apparatus by oversampling along the axial direction by translating the bed by a distance less than the height of a ring. A bed translation of an half or a quarter the height of a ring will allow to double or quadruple the number of axial translation symmetries in the apparatus.

Figure 6:
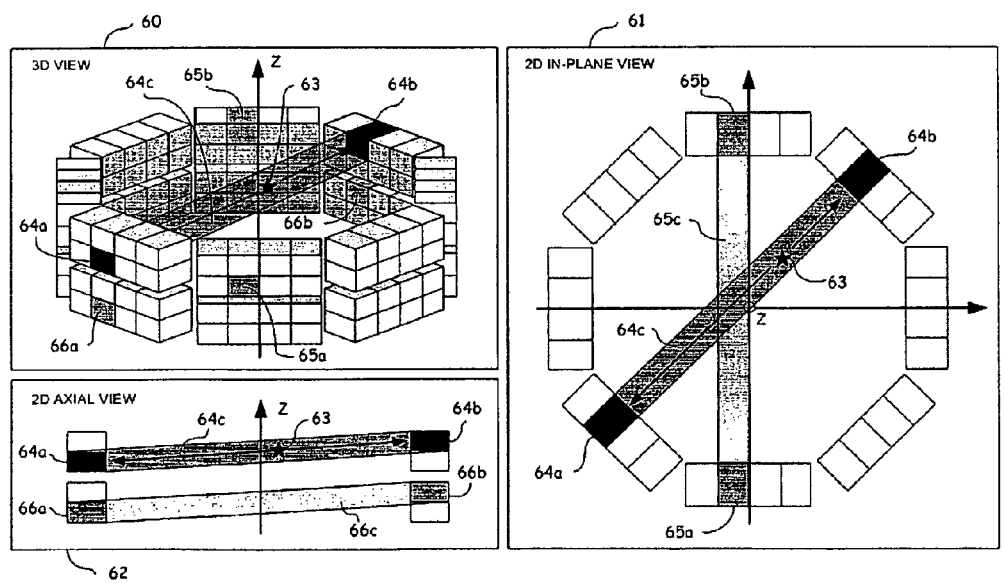
FIG. 6 is a pictorial view of all available symmetries between the TORs of an imaging system made of 4×2 crystal blocks that are repeated eight times around the ring and two times axially.

Although the aspect of maximizing the number of system symmetries is advantageous according to some aspects of the present invention, other aspects, like for example, the detection efficiency, the packaging constraints, the assembly constraints and the production cost, should also be considered during the conception. In regards to those aspects, a perfect symmetry imaging system may not be the most desirable system. Therefore, in some embodiments, the detector rings of the imaging system can be made from blocks of stacked detecting element (usually crystals) that are repeated around the rings and repeated in the axial direction (z-axis) in order to cover the desired FOV. A pictorial view of an imaging system made of 4×2 crystal blocks, repeated eight times around the ring and two times axially, is illustrated in FIG. 6. An example of a PET event 63 detected by the TOR 64c formed by the coincident detectors 64a and 64b is shown in a 3D view 60, a 2D in-plane view 61 and a 2D axial view 62. It is shown in the 2D in-plane view 61 that the TOR 65c (formed by detectors 65a and 65b) will have the same response function that the TOR 64c (formed by detectors 64a and 64b) because of in-plane rotation symmetries between detector blocks. For an apparatus made of blocks of detectors, the total number of in-plane rotation symmetries will be equal to the number of blocks within the ring. The blocks of detectors repeated axially will also lead to some axial symmetries between the TORs of different projection planes. The 2D axial view 62 shows that the TOR 66c formed by the detectors 66a and 66b will have the same response function than the TOR 64a formed by the detectors 64a and 64b. It this case, the maximum number of axial translation symmetries will be equal to the number of blocks repeated in the axial direction. Accordingly, in the non-restrictive illustrative embodiment of the present invention, many blocks made of few detectors should be used in order to preserve as many symmetries as possible in the imaging system.

Figure 7:
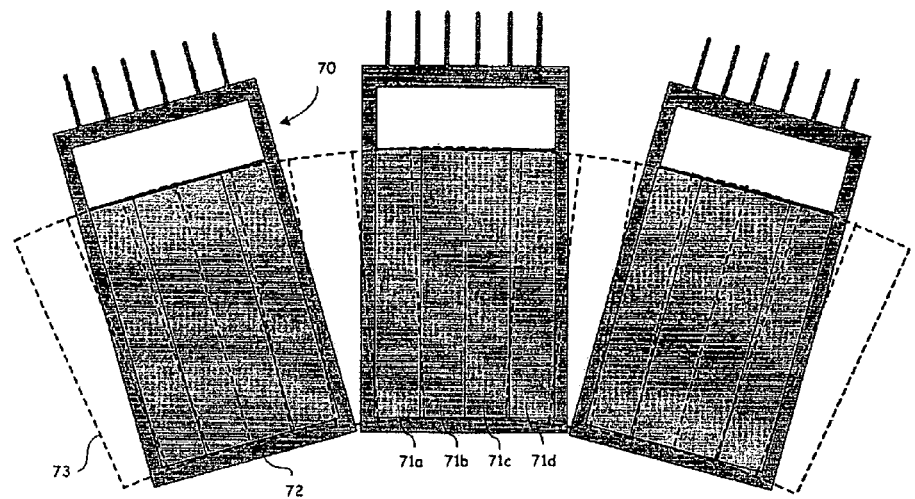
FIG. 7 is a pictorial view of a strategy for positioning detector blocks within an imaging system ring in such a way that the number of in-plane angular symmetries can be increased "artificially" using some approximations.

When detector rings are composed of many blocks made of few detectors, it is also possible to make some approximations in order to increase "artificially" the number of system symmetries. An example of such an approximation is illustrated in FIG. 7. In this figure, the detector blocks 70 are positioned uniformly around the ring in such a way that a gap of approximately one crystal width separates two detector blocks 70. A non-negligible gap between detector blocks is often due to the thickness of a casing material 72 protecting the detectors. In order to increase the number of in-plane symmetries in the system, one could assume that the detectors are positioned according to a detector ring with ideal in-plane symmetries (dotted grid 73). This approximation could in turn lead to a significant system matrix size reduction and to faster image reconstructions. Most important errors in the system matrix will come from the TORs made with crystals at position 71a and 71d which diverge more from the ideal detector grid 73.

Figure 8:
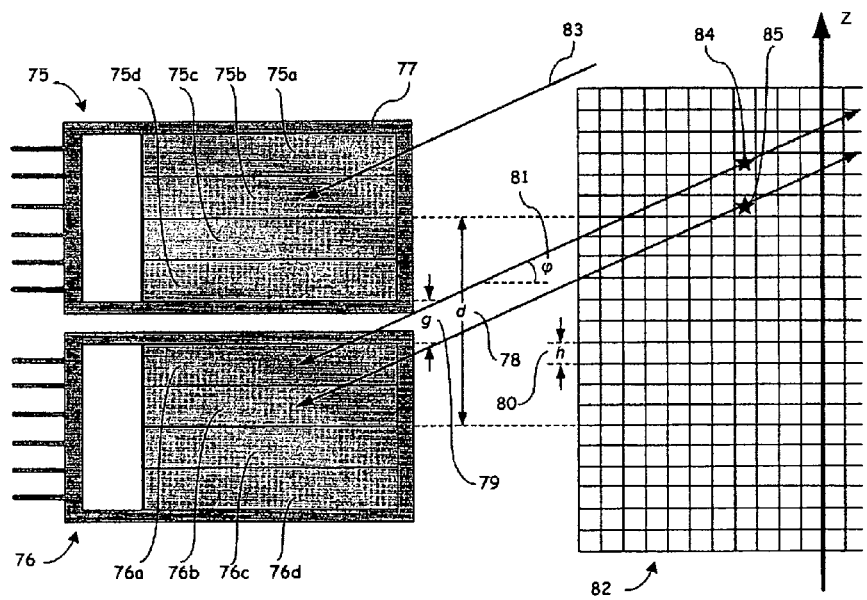
FIG. 8 is a pictorial view of a strategy for positioning two detector blocks in the axial direction and choosing the image representation in such a way that the number of axial symmetries can be increased "artificially" using some approximations.

A careful positioning of blocks of detector in the axial direction can also leads to an increase of the number of axial symmetries. As an example, an 8-ring camera made from two detector blocks (75, 76) each having four crystals axially (75a-75d, 76a-76d) is shown in FIG. 8. By choosing a gap 79 of one crystal height between the bottom crystal 75d of the top block 75 and the top crystal 76a of the bottom block 76, the camera can be viewed as a 9-ring camera with perfect axial symmetries. A non-negligible gap 79 is often required due to the presence of a casing material 77 protecting the detectors. In order to preserve the axial symmetries during the computation of the system matrix, the image grid 82 should be selected carefully so that the height of a voxel 80 is an integer fraction of the distance between two symmetric projection planes which is equal to the distance between two blocks 78 unless the camera is approximated by a 9-ring configuration leading to one detector height (or the gap 79). The approximation of an 8-ring camera by a 9-ring camera with perfect axial symmetries could lead to some error in the system matrix. In fact, two photons 84 and 85 impinging respectively on crystals 76a and 76b at the same entrance point will not travel through the same quantity of matter and thus, will not result in the same probability of being absorbed. In contrast, using only axial symmetries between blocks, it can be seen that the two photons 83 and 85 impinging respectively on crystals 75b and 76b will have the same probability of being absorbed.

According to one aspect of the non restrictive illustrative embodiment of the present invention, an imaging system having many symmetries is built in order to optimize the performance of the image reconstruction methods. Nevertheless, it is to be understood that the image reconstruction methods according to the non restrictive illustrative embodiment of the present invention could be adapted to any imaging system even if it has few symmetries.

Once the architecture and the geometries of the imaging system have been selected, the next step consists in defining a two-dimensional (2D) or a three-dimensional (3D) image discretized with basis functions that are selected and positioned on a polar or cylindrical coordinate grid in order to preserve the system symmetries during the computation of the system matrix coefficients. To reach this goal, the basis functions $b_j(x, y, z)$ of equation 5, which were defined according to a Cartesian coordinate grid, are replaced by a basis function $b_j(r, \theta, z)$ defined in a polar or cylindrical coordinate grid $(r, \theta, z)$, where r is the distance from the center of the image, $\theta$ is the angle made with the x-axis of the Cartesian image and z is the axial position being equivalent to the z-axis of the Cartesian image. The relation between the cylindrical coordinate basis function $b_j(r, \theta, z)$ and the continuous image representation $f(x, y, z)$ can be stated as:

$$\bar{f}(x, y, z) = T_{pc} \sum_{j=1}^{B} \bar{f}_j b_j(r, \theta, z) \quad (9)$$

where $T_{pc}$ denotes a polar-to-Cartesian transformation. The matrix $T_{pc}$ can also be used to convert a cylindrical image into a Cartesian image:

$$\sum_{i=1}^{B_C} \bar{f}_i^{(c)} b_i(x, y, z) = T_{pc} \sum_{j=1}^{B_P} \bar{f}_j^{(p)} b_j(r, \theta, z) \quad (10)$$

where the number of voxels $B_c$ in the Cartesian image do not have to be equal to the number of voxels $B_p$ in the cylindrical image and where $\bar{f}_i^{(c)}$ and $\bar{f}_j^{(p)}$ denotes respectively the $i^{th}$ and $j^{th}$ voxel values of the Cartesian and cylindrical images.

Figure 9:
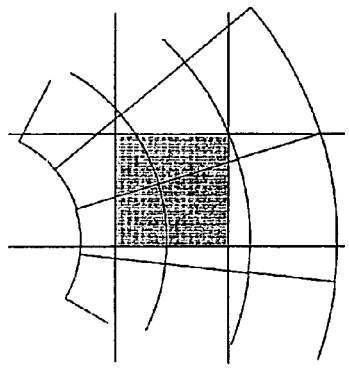
FIG. 9 is a representation of a polar-to-Cartesian transformation where weight contribution of every polar pixels to the square pixel is set according to the ratio of the polar pixel area falling inside the square pixel divided by the total polar pixel area.

The operation of converting a polar or cylindrical image into a Cartesian image is quite fast since the transformation matrix $T_{pc}$ is really sparse and can be defined for only one 2D image slice. Only the few polar pixels that fall completely or partly inside the region delimited by the square pixel will contribute to the square pixel estimate leading to:

$$\bar{f}_i^{(c)} = \sum_{j=1}^{M_i} w_{i,j} \bar{f}_{index_i(j)}^{(p)} \text{ for } i = 1, \ldots, B_c \quad (11)$$

where $M_i$ are the numbers of polar pixels that have a non-null contribution to the $i^{th}$ Cartesian pixel and $w_{i,j}$ is the weighted contribution of every $j^{th}$ non-null polar pixels that are accessed through an index vector $index_i$ which is specific to the $i^{th}$ Cartesian pixel. An example of polar pixels having non-null contributions to a Cartesian square pixel is illustrated in FIG. 9. The weighting value of every polar pixel will be set according to the ratio of the polar pixel area falling inside the square pixel divided by the total polar pixel area. However, other methods could also be required to find the polar pixel weighting values given, for example, that the polar image representation is based on overlapping pixels.

The basis functions $b_j(r, \theta, z)$ used in the said polar or cylindrical image can be overlapping and/or can be of different shape, as long as the step of computing the system matrix coefficients preserved the symmetries (or redundancies) in the system matrix. For example, in a two-dimensional polar image representation, the pixels can have a shape similar, but not restricted to, a pie shape, a truncated pie shape, a circle, a blob, a square or a rectangle. For a three-dimensional cylindrical image representation, the voxels can have a shape similar, but not restricted to, a pie shape volume, a truncated pie shape volume, a cylindrical volume, a sphere, a blob, a cube or a rectangular volume.

The computation of the system matrix coefficients $a_{i,j}$ (equation 7) for a given imaging system and according to a polar or cylindrical image representation (equation 9) could be performed using different methods. It is to be understood that the method should be adapted to the physical aspects of the imaging system modality, to the geometry, shape and properties of the detector ring elements of the imaging system and to the grid and basis functions used in the polar or cylindrical image representation. Moreover, a more or less accurate model of the different aspects of the acquisition process can be included or not in the system matrix computation. For example, in PET, a system matrix can include or not a model of, the positron range, the attenuation, the random events and/or the scatter events. The computation of the system matrix coefficients can be based on an analytical model and/or on Monte Carlo simulations. Some simpler and/or faster methods can also be used and be more appropriate while using, for example, on-the-flag computation of the system matrix coefficients during the image reconstruction procedure. One should notice that the reduction of the system matrix size through the use of system symmetries, according to some aspects of the non-restrictive illustrative embodiment of the present invention, would reduce the computation burden of computing the system matrix coefficients by a factor equivalent to the number of symmetries.

In order to preserve the maximum number of symmetries during the probability matrix computation, the geometries of the polar or cylindrical image should correspond to the geometries of the imaging system. The total number of TORs measured by a three-dimensional imaging system, denoted by N, can be decomposed in several parts:

$$N = (N_\theta \cdot N_q) \cdot (N_\phi \cdot N_p - \alpha) \quad (12)$$

where $(N_\theta \cdot N_q)$ are the total number of TORs in one projection plane and $(N_\phi \cdot N_p - \alpha)$ are the total number of projection planes measured by the apparatus. More precisely, $N_\theta$ and $N_q$ are respectively the number of symmetric and non-symmetric TORs in one projection plane, $N_\phi$ and $N_p$ are respectively the number of symmetric and non-symmetric projection planes and $\alpha$ is a correction factor to take into account the fact that the cross-X projection planes will have less symmetries than the direct projection planes. This fact was presented previously in FIG. 4 which illustrates all the different projection planes of a 4-ring apparatus. In this example, the number of axial symmetries is equal to the number of rings, giving $N_\phi = 4$, and the number of non-symmetric projection planes is $N_p = 4$ ($\alpha = 0$) when mirror symmetry are used and $N_p = 7$ ($\alpha = 12$) when they are not.

The total number of voxels in a three-dimensional image based on a polar coordinate grid can also be decomposed in several parts:

$$B = (B_\theta \cdot B_r) \cdot (B_\phi \cdot B_z) \quad (13)$$

where $(B_\theta \cdot B_r)$ are the total number of voxels in one 2D image slice parallel to the r$\theta$-plane and $(B_\phi \cdot B_z)$ are the total number of 2D image slices along the z-axis. More precisely, $B_\theta$ is the number of angular symmetries in the 2D image slice and $B_r$ is the number of independent (or non-symmetric) voxels which could not be obtained by an image rotation, $B_\phi$ and $B_z$ are respectively the number of voxels along the z-axis which are symmetric and non-symmetric according to the positioning of the detector rings along the z-axis.

Figure 10:
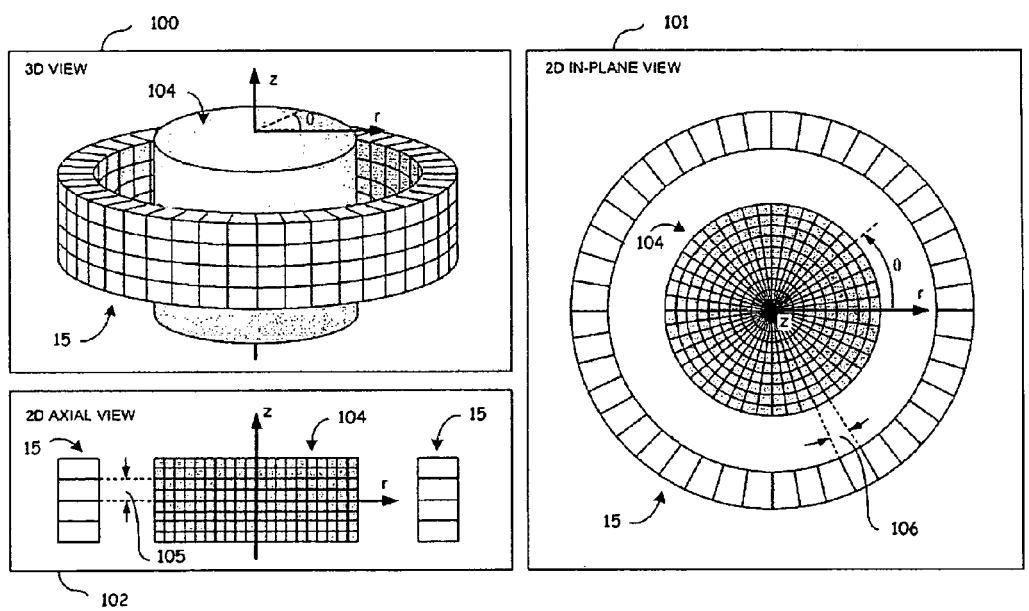
FIG. 10 is a pictorial view of a three-dimensional imaging system and an image representation based on a cylindrical coordinates grid dedicated for a 4-ring camera with perfect symmetries.

An example of a three-dimensional image 104 based on a cylindrical coordinate grid dedicated for a 4-ring camera 15 with perfect symmetries is shown in FIG. 10. It can be seen in the 2D in-plane view 101 that the number of angular symmetries $B_\theta$ in the polar image 104 corresponds to the number of in-plane angular symmetries $N_\theta$ in the detector rings 15. In this example, the number of voxels at each radius position is equal to $B_\theta$ leading to a number of non-symmetric voxels $B_r$ in one 2D image slice that is equal to the number of radius positions. Referring to the 2D axial view 102, the height 106 of the voxels is selected to be an integer fraction of the distance 107 between two symmetric projection planes so that the number of symmetric voxels along the z-axis $B_\phi$ is equal to the number of axial symmetries $N_\phi$ in the apparatus. The number of non-symmetric voxels along the z-axis $B_z$ will correspond to the number of voxels comprised within the distance 107 between two symmetric projection planes.

More generally, in the non restrictive illustrative embodiment of the present invention, the number of angular symmetries $B_\theta$ in the polar or cylindrical image should be set equal or be a multiple of the number of in-plane symmetries $N_\theta$ in the imaging system, giving $B_\theta = k \cdot N_\theta$, where k is an integer higher than zero. Under certain conditions where $N_\theta$ is really high, a number of angular symmetries $B_\theta$ lower than $N_\theta$ can be selected in order to avoid very small pixel area (or voxel volume) in the middle of the image. The quality of the image obtained with some image reconstruction methods can be affected somehow by the presence of very small pixel area (or voxel volume).

Figure 11:
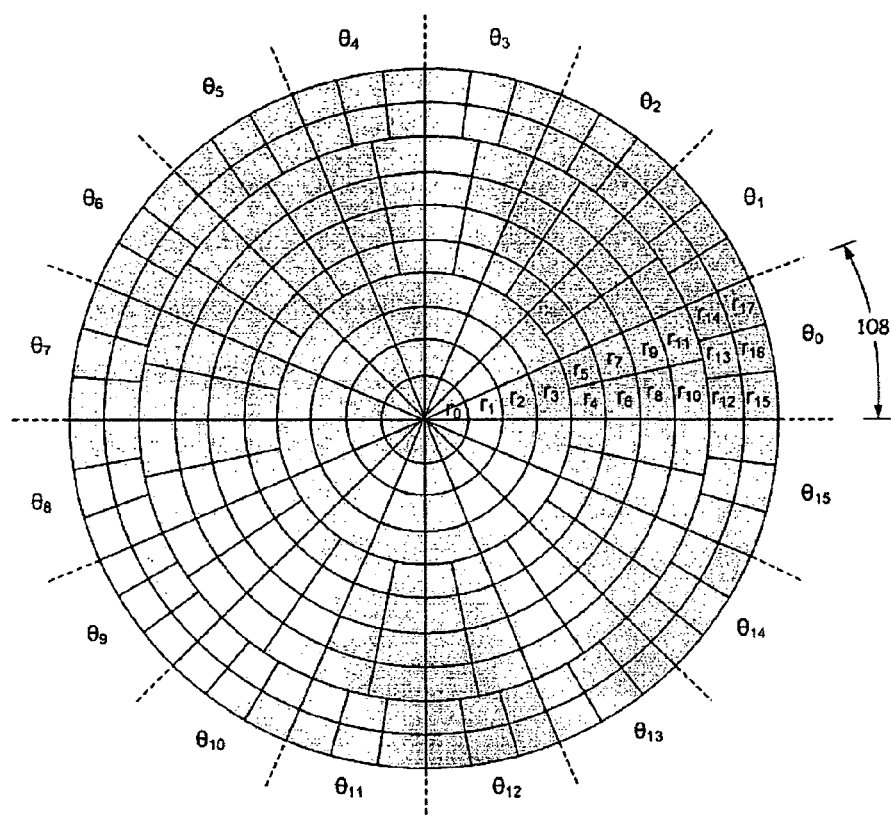
FIG. 11 is a pictorial view of a polar image representation having more pixels at radius position farther from the image center in order to achieve a better uniformity between the pixel area (or voxel volume) and still preserving the block circulant structure of the system matrix.

Once the number of image angular symmetries $B_\theta$ is set, the number of voxels at each radius position will be equal or be an integer multiple of $B_\theta$. In the example of FIG. 10, the same number of voxels, equal to $B_\theta$, were used at each radius position. However, a better uniformity between the pixel area (or voxel volume) could be achieved by using more pixels at radius position farther from the image center. An example of such an image representation is illustrated in FIG. 11. In this case, the number of non-symmetric pixels $B_r$ will be equal to the number of different pixels within one symmetric angular span 108, leading to $B_r = 18$.

In order to preserve the maximum number of axial symmetries in the imaging system, the number of axial symmetries $B_\phi$ in the cylindrical image should be set equal to the number of axial symmetries in the apparatus $N_\phi$. The optimal setting for $B_\phi$ can also be higher than $N_\phi$ in some cases where multiple acquisition frames taken at different bed positions are used to extend the axial FOV of the measurements. The number of non-symmetric voxels $B_z$ in the axial direction depends on the distance between two symmetric image slices (or projection planes) and on the minimal voxel height required to preserve the spatial resolution of the apparatus.

Another broad aspect of the non restrictive illustrative embodiment of the present invention consists of restructuring the system matrix A into a block circulant matrix. A block circulant system matrix can be obtained given that the projection data $\bar{y}$ and the image voxels $\bar{f}$ are ordered in a particular order. This will first be demonstrated for two-dimensional imaging problems. Additional considerations for three-dimensional imaging problems will then be presented.

For two-dimensional image reconstruction problems, $N_\phi$, $N_p$, $B_\phi$ and $B_z$ are useless since the third dimension, which is parallel to the axial direction (z-axis), is not considered. The number of symmetries or equivalently the number of blocks in the block circulant system matrix, denotes here by $S_\theta$, will be fixed by the smallest value between $N_\theta$ and $B_\theta$. In other words, the number of blocks will be equal to the number of in-plane symmetries $N_\theta$ in the imaging system unless the number of angular symmetries $B_\theta$ in the polar image is less. Each block of the block circulant probability matrix will be a n×m matrix where n is the number of rows being equal to the number of TORs divided by the number of blocks, giving $n = (N_\theta \cdot N_q)/S_\theta$, and m is the number of column being equal to the number of pixels divided by the number of blocks, giving $m=(B_\theta \cdot B_r)/S_\theta$. To obtain a block circulant system matrix, the measurement vector $\bar{y}$ should be ordered according to $\bar{y}=\{\bar{y}_{i,j}: i=1, \ldots, S_\theta; j=1, \ldots, n\}$ and the image pixel vector according to $\bar{f}=\{\bar{f}_{i,j}: i=1, \ldots, S_\theta; j=1, \ldots, m\}$ where the subscript j vary faster then the subscript i. In other words, the measurement and image vectors are ordered in $S_\theta$ groups of respectively n and m data stored in contiguous memory locations.

Figure 12:
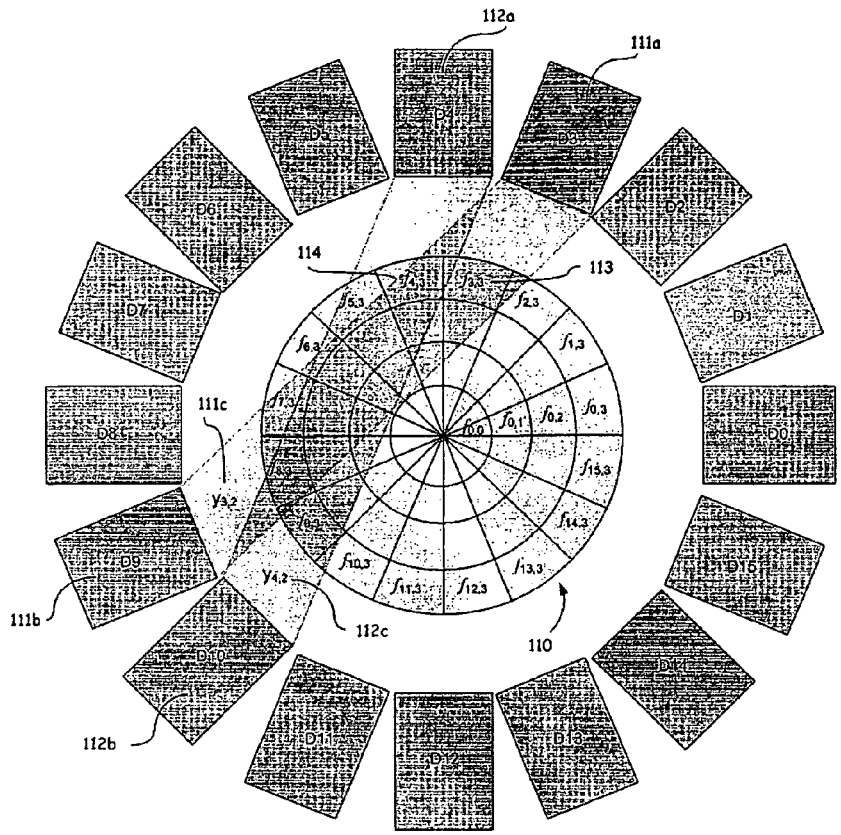
FIG. 12 is a pictorial view of a fairly simple imaging system with a polar image representation that is used to illustrate how a block circulant system matrix can be derived from a polar or cylindrical image representation.
Figure 13:
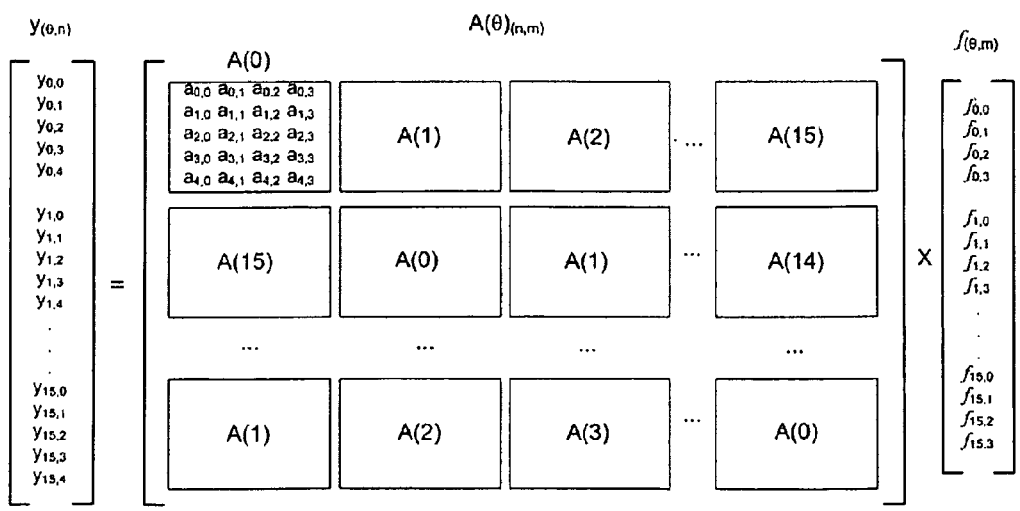
FIG. 13 is a block circulant system matrix that can be obtained using the imaging system representation in FIG. 12.

As an example, a pictorial view of a fairly simple imaging system with a polar image representation is shown in FIG. 12 and the corresponding block circulant system matrix is shown in FIG. 13. Referring to FIG. 12, it can be seen that the orientation of the pixel $f_{3,3}$ 113 according to the TOR $y_{3,2}$ 111c will be the same as the orientation of the pixel $f_{4,3}$ 114 according to the TOR $y_{4,2}$ 112c and therefore, both pixels will have the same probability of contributing to the number of counts of their respective TORs. The repetitions between the matrix coefficients of symmetric pixel-TOR combination will lead to a block circulant matrix having $S_\theta=N_\theta=B_\theta=16$ block matrices of size n×m (FIG. 13). In this example, the number of non-symmetric TORs is equal to the number of bins, leading to $n=N_q=5$, and the number of non-symmetric pixels is equal to the number of radius positions, leading to $m=B_r=4$.

When the image reconstruction problem is extended to three dimensions, the size of the system matrix A can grow rapidly since both the number of measured TORs and the number of voxels are increased. The number of measurements is increased by the number of projection planes measured by the apparatus which is equal to $(N_\phi \cdot N_p - \alpha)$ (equation 12). The number of voxels in the image is increased by the number of 2D images slices (voxels along the z-axis) required to cover the whole FOV which is equal to $(B_\phi \cdot B_z)$ (equation 13). The size growth of the 3D probability matrix can however be minimized by taking advantage of the axial symmetries between the projection planes of the imaging system. This leads to two different strategies for restructuring the three-dimensional probability matrix into a block circulant matrix.

The first strategy consists of using only the in-plane symmetries of the 3D imaging system to obtain a block circulant system matrix with a similar structure than the one obtain for 2D problems. The number of circulant matrix blocks, denoted by $S_\theta$, will be fixed by the smallest value between $N_\theta$ and $B_\theta$. The dimension n×m of each block will however be larger than for 2D image reconstruction problems, the total number of TORs being equal to N (equation 12), leading to $n=N/S_\theta$ and the total number of voxels being equal to B (equation 13), leading to $m=B/S_\theta$. A block circulant matrix can then be obtained by ordering the measurement vector $\bar{y}$ according to $\bar{y}=\{\bar{y}_{i,j}: i=1, \ldots, S_\theta; j=1, \ldots, n\}$ and the image voxel vector according to $\bar{f}=\{\bar{f}_{i,j}: i=1, \ldots, S_\theta; j=1, \ldots, m\}$ where the subscript j vary faster then the subscript i.

The second strategy consists of using both the in-plane and the axial symmetries of the 3D imaging system in order to obtain a block circulant system matrix where the blocks are themselves made of block circulant matrices. This new system matrix formulation is called here a double block circulant matrix. The $S_\phi \times S_\phi$ bigger circulant matrix blocks comes from the axial symmetries in the system and $S_\phi$ will therefore be fixed by the smallest value between $N_\phi$ and $B_\phi$. Each big block will be a $S_\theta \times S_\theta$ block circulant matrix arising from the in-plane symmetries, where $S_\theta$ is fixed by the smallest value between $N_\theta$ and $B_\theta$. Each block of the $S_\theta \times S_\theta$ block circulant matrix will be a n×m matrix where $n=(N_\theta \cdot N_q \cdot N_\phi \cdot N_p)/(S_\phi \cdot S_\theta)$ and $m=B/(S_\phi \cdot S_\theta)$. To obtain the double block circulant system matrix, the camera measurement vector should be ordered according to $\bar{y}=\{\bar{y}_{i,j,k}: i=1, \ldots, S_\phi; j=1, \ldots, S_\theta; k=1, \ldots, n\}$ and the image voxel vector according to $\bar{f}=\{\bar{f}_{i,j,k}: i=1, \ldots, S_\phi; j=1, \ldots, S_\theta; k=1, \ldots, m\}$ where the subscript k vary faster then the subscript j and i. In other words, the measurement and image vectors are ordered in $S_\phi$ groups each containing $S_\theta$ sub-groups of respectively n and m data stored in contiguous memory locations.

Figure 14:
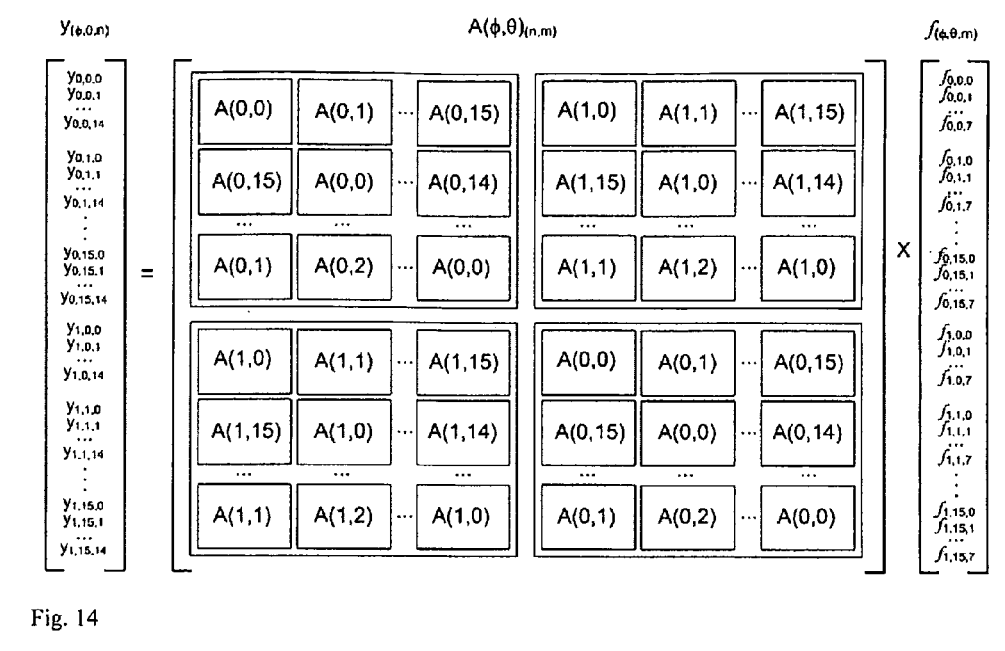

An example of a double block circulant system matrix obtained for a 3D imaging system is represent in FIG. 14. The system matrix was defined for the system configuration shown in FIG. 12, given that the camera is composed of two rings of detectors and that the 3D image is composed of 4 slices in the axial direction. This imaging system will lead to a double block circulant system matrix where the number of big blocks is equal to $S_\phi=N_\phi=B_\phi=2$, the number of small blocks is equal to $S_\theta=N_\theta=B_\theta=16$ and each small block is a n×m matrix with $n=N_q \cdot N_p=5 \cdot 3=15$, and $m=B_r \cdot B_z=4 \cdot 2=8$.

An advantage of using only in-plane symmetries to obtain a block circulant system matrix is that only the projection planes that were measured by the apparatus (equation 12) have to be included in the matrix. In contrast, when the axial symmetries are also used to obtain a double block circulant system matrix, every different projection planes $N_p$ should have the same number of axial symmetries $N_\phi$, leading to $N=(N_\theta \cdot N_q \cdot N_\phi \cdot N_p)$ (equal to equation 12 with $\alpha=0$). Using as an example the 4-ring camera shown in FIG. 4, a total of 16 projection planes are actually measured by the apparatus. However, when using the double block circulant matrix formulation, all the $N_p=7$ different projection planes (not using mirror symmetries) have the same number of axial symmetries $N_\phi=4$, giving a total of 28 projection planes instead of 16.

Figure 15:
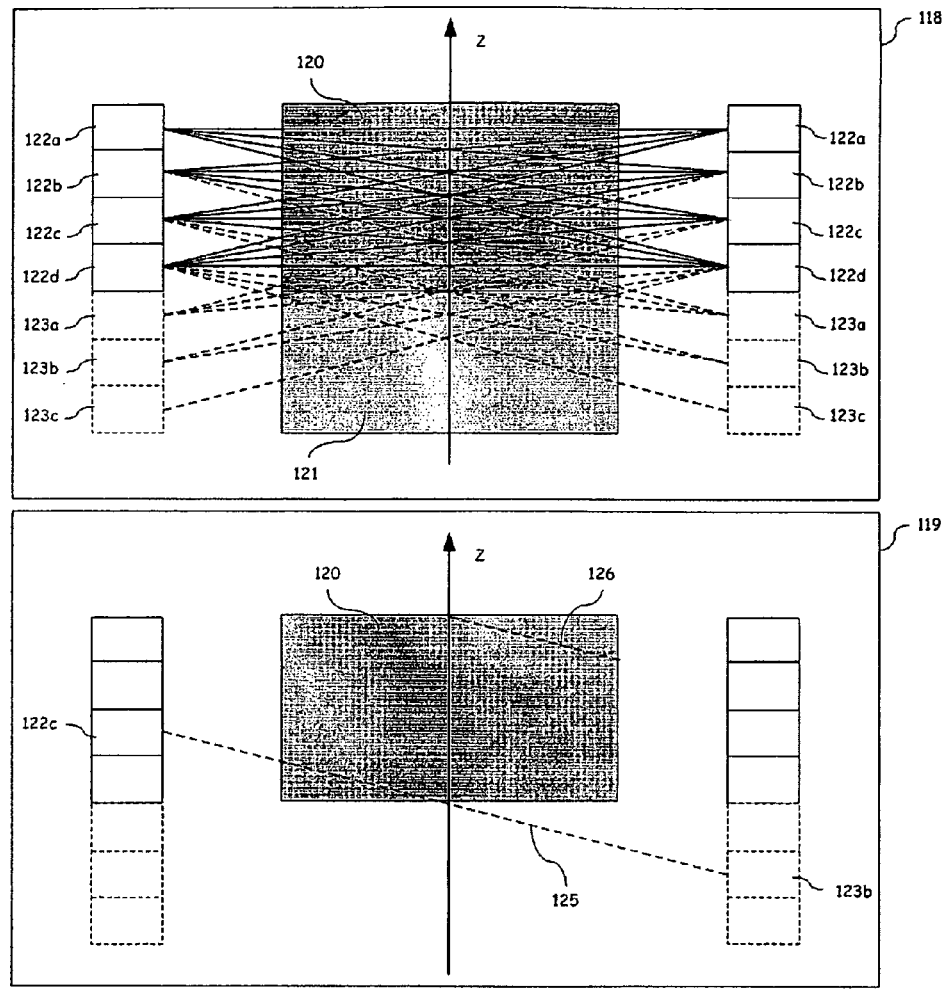
FIG. 15 is a pictorial view of all the measured projection planes (solid lines) and of all the unmeasured or "missing" projection planes (dotted lines) resulting from the constraint of using the same number of axial symmetries for all projection planes.

Another particular consideration when using a double block circulant system matrix is that the use of projection planes which partly fall outside the axial FOV of the reconstructed image can introduce errors in the modelization of the system matrix when those effects are not handle correctly. This phenomenon is illustrated in FIG. 15 which show a 4-ring apparatus where all the measured projection planes are represented by solid lines and all the unmeasured or "missing" projection planes, which result from the use of the same number of axial symmetries for all projection planes, are shown by dotted lines. In this figure, the 4 rings of the apparatus (122a, 122b, 122c and 122d) are drawn with a solid line and the "missing" rings (123a, 123b, 123c) issue from missing projection planes are drawn with dotted lines. One should notice that missing projection planes could be obtained by taking measurements at different bed positions along the z-axis. This method was illustrated in FIG. 5. In the state of the art, most image reconstruction methods use only the projection planes measured by the apparatus at a given bed position to reconstruct the 3D image 120. In this case, the height of the image 120 can be set equal to the axial FOV of the imaging system. However, one must also include the missing projection planes in the system matrix formulation in order to preserve the double block circulant structure of the system matrix. In such condition, using only the image 120 defined in between the axial FOV of the apparatus will result in some errors in the system matrix coming from a contamination of the portion of the missing projection planes that falls outside the image 120. In other words, the double block circulant structure of the system matrix will relate the portion of the missing projection planes exiting the bottom image slice 120 to the voxels at the top of the image 120. An example of a portion 125 of a missing projection plane 126 contaminating the reconstructed image 120 is illustrated in the view 128 of FIG. 15. A solution to this problem consists of extending the image 121 in such a way that the axial FOV include all the measured projection planes (122a, 122b, 122c and 122d) and all the missing projection planes (123a, 123b and 123c) imposed by the use of the double block circulant matrix. Another solution to this problem consists of estimating those missing projections by some means to equilibrate the system matrix equation.

In the non-restrictive illustrative embodiment of the present invention, the 3D measurements coming from different acquisition frames taken at different bed positions along the z-axis can lead to two broad strategies for reconstructing the whole volume of the object being imaged.

Figure 16:
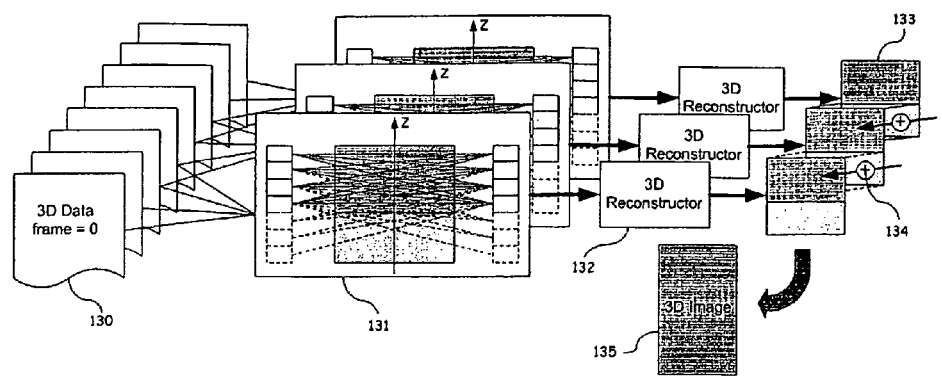
FIG. 16 is a pictorial view illustrating the main steps of a strategy for merging the measurements taken at different bed positions for the three-dimensional image reconstruction procedure.

A pictorial view illustrating the main steps of the first strategy is shown in FIG. 16. The first step consists of combining the information coming from acquisition frames 130 taken at different bed positions for obtaining a measurement vector that partly defines the whole 3D image to be reconstructed. A block circulant or a double block circulant system matrix 131, which relates the measurement vector $\bar{y}$ made from some merged acquisition frames 130 to the image vector $\bar{f}$ with a given axial height, is then used by a 3D image reconstructor 132 in order to reconstruct a partial volume 132 of the whole 3D image 135 to be reconstructed. The process of reconstructing partial volumes 132 of the 3D image 135 is repeated using acquisition frames 131 taken at different bed positions. All the partial 3D images 132 can then be added together 134 or recombined by some means in order to obtain the whole 3D image volume 135.

Figure 17:
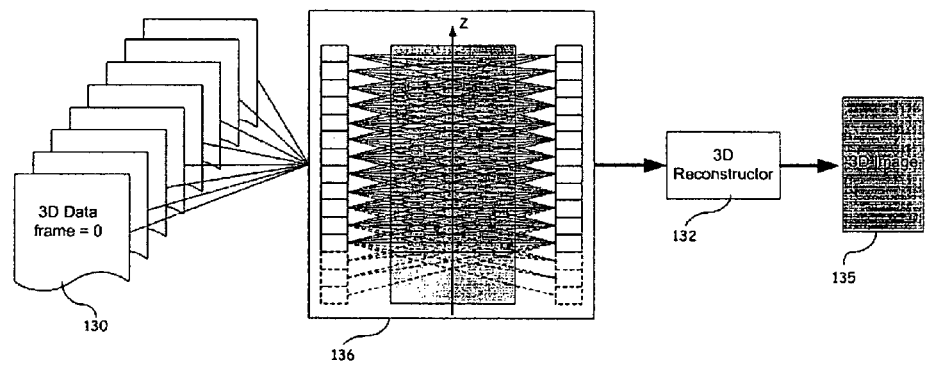
FIG. 17 is a pictorial view illustrating the main steps of another strategy for merging the measurements taken at different bed positions for the three-dimensional image reconstruction procedure.

A pictorial view of the second strategy for reconstructing an image using measurements taken at different bed positions is illustrated in FIG. 17. The first step consists of combining the information of all the acquisition frames 130 taken at different bed positions in order to obtain a measurement vector $\bar{y}$ that fully cover the whole 3D image FOV to be reconstructed. A block circulant or a double block circulant system matrix 136, which relates the measurement vector $\bar{y}$ of all the acquisition frames 130 being merged to the image vector $\bar{f}$ covering the whole FOV, is then used by a 3D image reconstructor 132 in order to reconstruct the whole 3D image 135 volume.

Referring to the FIG. 8, it is important to mention that the strategy of taking measurements at different bed positions to increase the number of axial system symmetries can still be used for cases where the axial gap 79 between the detector blocks is not an integer fraction of the distance 78 between two symmetric projection planes. For example, by translating the bed in the axial direction by a distance $t_{bed}$ equal to an integer fraction of the distance d 78 between two symmetric projection planes, leading to $t_{bed}=d/k$ where k is an integer, will also allow the overlap of some projection planes coming from acquisition frames taken at different bed positions. However, since not all of the projection planes will overlap perfectly, the number of different projection planes in the extended data set (131 in FIG. 16 or 136 in FIG. 17) will be increased by a factor equal to k and the system matrix size will also be increased by this factor. One should notice that measurements taken while performing a continuous bed motion can also be sorted into bed acquisition frames with k being high enough to prevent from loosing spatial resolution in the axial direction.

According to some aspects of the present invention, other kinds of bed displacements, like wobble bed motions or helical CT scans, can also be used by the image reconstruction methods. When performing an acquisition with wobble bed motions, the same system matrix A can be used to reconstruct the image corresponding to each wobble position. For direct image reconstruction methods, the images can be reconstructed independently and then be merged together according to their respective wobble positions. For iterative methods, the merging of the images can be performed at each iteration loop before the step of updating the image estimate so that the maximum information is used by the iterative algorithm. An independent image for each wobble bed position can then be obtained from the image estimate in order to perform the forward projection step of the next iteration loop. When performing an helical CT scan, the z-axis of the cylindrical image representation can be modified in order to preserve the symmetries in the system. For example, instead of using a cylindrical image representation with all image slices being aligned together, each successive 2D image slices can have a rotation phase difference which follows the helical movement of the CT scan.

Real Time Image Reconstructor

In the non-restrictive illustrative embodiment of the present invention, a real time image reconstructor based on the pseudo-inversion of a block circulant system matrix by the use of singular value decomposition (SVD) is provided to reconstruct a two-dimensional or a three-dimensional image. The method can be decomposed in five main steps: 1) perform the SVD decomposition on the block circulant system matrix in the Fourier domain, 2) use the SVD components, which are the singular values and the singular vectors to compute the pseudo-inverse $A^+$ of the system matrix, 3) perform in the Fourier domain a matrix-vector product between the pseudo-inverse matrix $A^+$ and the measurement vector $\bar{y}$ to obtain the image vector $\bar{f}$ in the Fourier domain and 4) perform the inverse Fourier transform on the image vector $\bar{f}$ and 5) apply a polar-to-Cartesian transformation on the polar or cylindrical image to obtain an image that can be displayed on a conventional display. Different variations in every step of this procedure are possible leading to new algorithms having some advantages and some drawbacks. It is to be understood that it is within the scope of the present invention to include all the possible variations present in every step of the image reconstruction procedure and not to be limited to the algorithms issued from some combination of options, which are presented as example only.

The first step of the real time image reconstruction method of the non-restrictive illustrative embodiment of the present invention consists of using the singular value decomposition to decompose the imaging system probability matrix A into its singular values D, its left singular vectors U and its right singular vectors V, leading to:

$$A = UDV^T \quad (14)$$

where $U=\{u_{ij}: i=1, \ldots, N; j=1, \ldots, B\}$ and $\{V=v_{ij}: i=1, \ldots, B\}$ are orthogonal matrices, $D=\text{diag}(\mu_1, \mu_2, \ldots, \mu_B)$ is a diagonal matrix containing the singular values, which are usually ordered so that $\mu_1 \geq \mu_2 \geq \ldots \geq \mu_B \geq 0$. Performing the SVD decomposition directly on the system matrix A is equivalent to some methods of the prior art proposed by Shim [Shim, "SVD Pseudoinversion image reconstruction, 1981] and by Selivanov [Selivanov, "Fast PET image reconstruction based on SVD decomposition of the system matrix]. The main drawback of those methods is the computational burden associated to the SVD operation when applied to large system matrices. In the non-restrictive illustrative embodiment of the present invention, the block circulant system matrix is transformed in the Fourier domain in order to accelerate the SVD procedure. Accordingly, the block circulant system matrix A can be expressed as:

$$A = (\Im_\theta \otimes I_n)^H \Lambda (\Im_\theta \otimes I_m) \quad (15)$$

where $\mathfrak{I}_\theta$ is a normalized $S_\theta \times S_\theta$ discrete Fourier transform operator matrix with $w^k = \exp^{-j2\pi k/S_\theta}$:

$$\mathfrak{I}_\theta = \frac{1}{\sqrt{S_\theta}} \begin{bmatrix} 1 & 1 & 1 & \ldots & 1 \\ 1 & w^1 & w^2 & \ldots & w^{S_\theta-1} \\ 1 & w^2 & w^4 & \ldots & w^{2(S_\theta-1)} \\ \vdots & \vdots & \vdots & & \vdots \\ 1 & w^{S_\theta-1} & w^{2(S_\theta-1)} & \ldots & w^{(S_\theta-1)(S_\theta-1)} \end{bmatrix} \quad (16)$$

and $\Delta$ is a $S_\theta \cdot n \times S_\theta \cdot m$ complex block-diagonal matrix where each of the $S_\theta$ blocks are $n \times m$:

$$\Delta = \begin{bmatrix} [\Delta_1] & & & [0] \\ & [\Delta_2] & & \\ & & \ddots & \\ [0] & & & [\Delta_{S_\theta}] \end{bmatrix} \quad (17)$$

and $I_n$ and $I_m$ are respectively $n \times n$ and $m \times m$ identity matrices, $\otimes$ is the Kronocker product and the subscript H is the Hermitian transpose (or conjugate transpose).

For two-dimensional image reconstruction problems, it has been shown that the system matrix A based on a polar image can be reordered into a block circulant matrix having $S_\theta$ block matrices of dimension $n \times m$ where $n=(N_\theta \cdot N_q)/S_\theta$ and $m=(B_\theta \cdot B_r)/S_\theta$. A single block circulant system matrix A can also be obtained for three-dimensional image reconstruction problems given that only the $S_\theta$ in-plane system symmetries are used. The dimension $n \times m$ of each block matrices will be in this case equal to $n=N/S_\theta$ and to $m=B/S_\theta$.

Once the block circulant system matrix A have been diagonalized into $\Delta$ using equation 14, the singular values and the singular vectors of A can be obtained by performing $S_\theta$ independent SVD decomposition on every $n \times m$ block matrices of the complex block-diagonal matrix $\Delta$. Performing $S_\theta$ different SVD operations on $n \times m$ complex matrices is many order faster than performing a single SVD operation on a bigger $S_\theta \cdot n \times S_\theta \cdot m$ matrix. The SVD decomposition can be performed on the small $n \times m$ complex matrices using the well known Golub-Kalahan algorithm or with some other methods. Another solution consists of performing the SVD decomposition on the whole complex block-diagonal matrix $\Delta$ by using the Fourier transform to accelerate matrix-vector and/or matrix-matrix operations required by many SVD procedures like for example, but not limited to, trace minimization methods, subspace iteration methods and single or block Lanczos methods.

Acceleration of the SVD decomposition of a block circulant matrix have already been applied to tomographic image reconstruction problems [Baker, "Generalized approach to inverse problems in tomography: Image reconstruction for spatially variant systems using natural pixels", 1992]. However, the block circulant matrix was a blurring matrix $A^T A$ that was obtained using a natural pixel decomposition of the image. It was shown previously (equation 3) that the resolution of the system of equations using a blurring matrix leads to a different image reconstruction problem. The result of the matrix-vector product between the inverted blurring matrix and the measurement vector must be backprojected to obtain the reconstructed image. Moreover, the image reconstruction problem state with a blurring matrix is more ill-conditioned.

Using the result of the SVD procedure which are the singular values D and the singular vectors U and V, it is possible to find the system matrix A pseudo-inverse by using:

$$A^+ = VD^+ U^T \quad (18)$$

where $A^+$ is the pseudo-inverse of A and $D^+$ is a diagonal matrix which contain the reverse of the singular values:

$$D^+ = \mathrm{diag}(1/\mu_1, 1/\mu_2, \ldots, 1/\mu_B) \quad (19)$$

When the SVD operation is performed on the block matrices of the block-diagonal matrix $\Delta$, the pseudo-inverse can be found by:

$$\Delta^+ = V_\Delta D_\Delta^+ U_\Delta^T = \begin{bmatrix} V_1 D_1^+ U_1^T & & & [0] \\ & V_2 D_2^+ U_2^T & & \\ & & \ddots & \\ [0] & & & V_{S_\theta} D_{S_\theta}^+ U_{S_\theta}^T \end{bmatrix} \quad (20)$$

where each of the $S_\theta$ block matrices have their own set of complex singular values and complex singular vectors. It could be advantageous to preserve the result of the SVD decomposition in the Fourier domain (as stated in equation 20) in order to accelerate matrix-vector multiplications between the system matrix pseudo-inverse and the measurement vector. Nevertheless, it is also possible to bring the result back in the space domain by substituting the pseudo-inverse $\Delta^+$ in equation 15:

$$A^+ = (\mathfrak{I}_\theta \otimes I_n)^H \Delta^+ (\mathfrak{I}_\theta \otimes I_m) \quad (21)$$

or equivalently:

$$V_A D_A^+ U_A^T = (\mathfrak{I}_\theta \otimes I_n)^H V_\Delta D_\Delta^+ U_\Delta^T (\mathfrak{I}_\theta \otimes I_m) \quad (22)$$

Moreover, one can notice that the singular values of the block-diagonal matrix $\Delta$, which are $D_\Delta = \{D_i : i = 1, \ldots, S_\theta\}$ with $D_i = \mathrm{diag}(\mu_1, \mu_2, \ldots, \mu_m)$, are real values that, when ordered in increasing order, are exactly the same as the singular values of the system matrix A, which are $D_A = \mathrm{diag}(\mu_1, \mu_2, \ldots, \mu_B)$. Thus performing truncation or some other operations on the singular values of $D_\Delta$ or of $D_A$ is equivalent.

The range of singular values for a real-world system matrix A can be very wide. Some singular values (they are presented as a nonincreasing sequence called singular value spectrum) can be very small (or even zeros). Thus, the condition number:

$$c = \frac{\max_k \mu_k}{\min_k \mu_k} \quad (23)$$

of the system matrix can be very high (even infinity if the matrix is singular). This ill-conditioning of the system matrix is the main reason why the pseudo-inverse can hardly be found directly even if A has the full rank. Moreover, the solution directly exploiting the pseudo-inverse would be very sensitive to noise. One simple regularization approach is the truncation of the singular value spectrum at some index T and removal of very small values $\mu_k$, $k=T+1, \ldots, B$ from the solution. Every coefficient $a_{ij}$ of the pseudo-inverse matrix $A^+$ can then be computed from:

$$a_{ij}^+ = \sum_{k=1}^{T} \frac{1}{\mu_k} U_{ik} V_{jk} \qquad (24)$$

Another regularization approach consists of reducing the influence of small singular values on the result by using individual weights $w_k$, k=1, ..., B, leading to:

$$a_{ij}^+ = \sum_{k=1}^{T} \frac{w_k}{\mu_k} U_{ik} V_{jk} \qquad (25)$$

where the weight $w_k$ applied to each singular value can be set according to some weighting functions. For example, the weighting function can be chosen to decrease the singular value spectrum according to a regularizer $\lambda$ such as:

$$w_k = \frac{\mu_k^2}{(\mu_k^2 + \lambda)} \qquad (26)$$

More complex methods can also be used to set an independent weighting factor for each pixel in the image. As an example, the equation 26 could be modified to include an independent regularizer $\lambda_i$ for every pixel of the image vector $\bar{I} = \{\bar{I}_i : i=1, \ldots, B;\}$ leading to a weighting function which depends both on the pixel and on the singular value:

$$w_{ik} = \frac{\mu_k^2}{(\mu_k^2 + \lambda_i)} \qquad (27)$$

In the non-restrictive illustrative embodiment of the present invention, a regularization approach which allows to use different sets of weighting functions for every pixels of the image, or at least for pixels at different radius positions in the polar or cylindrical image, could be required for cases where the pixel area (or voxel volume) varies significantly between the innermost and the outermost pixels or voxels. The disparities between the pixel areas (or volumes) will lead to a pseudo-inverse matrix $A^+$ having variation of noise amplification and spatial resolution between the innermost and the outermost pixels. This effect can be corrected by truncating (or by weighting) more abruptly the singular values for the innermost pixels then for the outermost pixels.

The third step of the image reconstruction procedure consists of performing the matrix-vector multiplications between the pseudo-inverse system matrix and the measurement vector. The matrix-vector operation is performed in the Fourier domain to reduce the number of operations. Accordingly, the pseudo-inverse matrix $\Delta^+$ or the SVD components $D_\Delta$, $V_\Delta$ and $U_\Delta$ can be used, leading to two broad class of image reconstruction procedures. For both procedures, the measurement vector is transformed in the Fourier domain before it is multiplied by the pseudo-inverse matrix and the result is transformed back in the spatial domain to obtain the reconstructed image, leading to:

$$\bar{I} = (\mathfrak{I}_\theta \otimes I_m)^H \Delta^+ ((\mathfrak{I}_\theta \otimes I_n) \bar{y}) \qquad (28)$$

or using the SVD components:

$$\bar{I} = (\mathfrak{I}_\theta \otimes I_m)^H V_\Delta D_\Delta^+ U_\Delta^T ((\mathfrak{I}_\theta \otimes I_n) \bar{y}) \qquad (29)$$

A polar-to-Cartesian conversion matrix $T_{pc}$, stated in equation 10, can then be applied to the polar or cylindrical image $\bar{I}$ to obtain a Cartesian image which can be shown on a conventional display.

It was stated in the previous section that for three-dimensional image reconstruction problems, it is also possible to use axial symmetries in order to obtain a $S_\phi \times S_\phi$ block circulant matrix where each block are themselves $S_\theta \times S_\theta$ block circulant matrices having blocks of dimension n×m. The size of the small n×m block matrices is set according to the number of projection data, giving $n = (N_\theta \cdot N_q \cdot N_\phi \cdot N_p)/(S_\phi \cdot S_\theta)$ and according to the number of voxels in the image, giving $m = B/(S_\phi \cdot S_\theta)$. The image reconstruction methods based on the SVD decomposition is then essentially the same except that the system matrix is diagonalized by applying two Fourier transform operator matrices:

$$A = (\mathfrak{I}_\theta \otimes I_{(n \cdot \phi)})^H P_\phi (\mathfrak{I}_\phi \otimes I_{(n \cdot \theta)})^H \Delta (\mathfrak{I}_\phi \otimes I_{(m \cdot \theta)})$$
$$P_\phi (\mathfrak{I}_\theta \otimes I_{(m \cdot \phi)}) \qquad (30)$$

where $\mathfrak{I}_\theta$ and $\mathfrak{I}_\phi$ are respectively the normalized $S_\theta \times S_\theta$ and $S_\phi \times S_\phi$ discrete Fourier transform operator matrix (equation 16), $\Delta$ is a $S_\phi \cdot S_\theta \cdot n \times S_\phi \cdot S_\theta \cdot m$ complex block-diagonal matrix where each of the $S_\phi \cdot S_\theta$ blocks are n×m (equation 17) and $I_{(n \cdot \phi)}$, $I_{(n \cdot \theta)}$, $I_{(m \cdot \phi)}$ and $I_{(m \cdot \theta)}$ are respectively $n \cdot S_\phi \times n \cdot S_\phi$, $n \cdot S_\theta \times n \cdot S_\theta$, $m \cdot S_\phi \times m \cdot S_\phi$ and $m \cdot S_\theta \times m \cdot S_\theta$ identity matrices, $\otimes$ is the Kronocker product and the subscript H is the Hermitian transpose (or conjugate transpose). One can also notice the presence of the permutation matrix $P_\phi$ which is applied after (or before) the direct (or inverse) $S_\theta \times S_\theta$ discrete Fourier transform operator to reorder the result into a block circulant matrix having $S_\phi$ blocks of dimension $S_\theta \cdot n \times S_\theta \cdot m$.

Computing the pseudo-inverse of the double block circulant matrix as stated in equation 30 will possibly lead to a valid solution for voxels at the center of the z-axis FOV. However, for 2D image slices at both extremum of the z-axis, the result will be perturbed by an incorrect modelization of the system matrix A coming from the use of the same number of axial symmetries $S_\phi$ for all projection planes. This problem was illustrated in FIG. 15. A solution to this problem consists of extending the image in the axial direction (z-axis) so that no projection planes are making a wrap-around in the beginning of the image (FIG. 15). This operation is equivalent to padding the double block circulant matrix with blocks of zeros leading to a $(S_\phi + p) \times (S_\phi + p)$ block circulant matrix made of $S_\theta \times S_\theta$ block circulant matrices where p is the number of padding blocks. Despite of the zero padding, the double block circulant structure provides many order acceleration both for the SVD decomposition procedure (equation 20) and for the matrix-vector product between the pseudo-inverse system matrix and the measurement vector. Another solution consists of estimating the value of those missing projection planes by some means.

Using the complex double block circulant system matrix (equation 30) with p padded blocks, an image vector $\bar{I}$ extended with $(p \cdot S_\theta \cdot m)$ zero data and a measurement vector $\bar{y}$ extended with $(p \cdot S_\theta \cdot n)$ zero data, the image can be reconstructed using the matrix pseudo-inverse $\Delta^+$:

$$\bar{I} = (\mathfrak{I}_{\theta} \otimes I_{(m \cdot \phi p)})^H (\mathfrak{I}_{\phi p} \otimes I_{(m \cdot \theta)})^H \Delta^+ ((\mathfrak{I}_{\phi p} \otimes I_{(n \cdot \theta)})$$
$$(\mathfrak{I}_\theta \otimes I_{(n \cdot \phi p)}) \bar{y}) \qquad (31)$$

or using the SVD components $D_\Delta$, $V_\Delta$ and $U_\Delta$:

$$\bar{I} = (\mathfrak{I}_\theta \otimes I_{(m \cdot \phi p)})^H (\mathfrak{I}_{\phi p} \otimes I_{(m \cdot \theta)})^H V_\Delta D_\Delta^+$$
$$U_\Delta^T ((\mathfrak{I}_{\phi p} \otimes I_{(n \cdot \theta)})(\mathfrak{I}_\theta \otimes I_{(n \cdot \phi p)}) \bar{y}) \qquad (32)$$

where $\mathfrak{I}_{\phi p}$ is the a normalized $(S_\phi + p) \times (S_\phi + p)$ Fourier transform operator, $I_{(n \cdot \phi p)}$ and $I_{(m \cdot \phi p)}$ are respectively $(n \cdot (S_\phi + p)) \times$ $(n \cdot (S_\phi + p))$ and $(m \cdot (S_\phi + p)) \times (m \cdot (S_\phi + p))$ identity matrices and where other variables are unchanged from the equation 30.

Another practical consideration when reconstructing a 3D image with a method based on a double block circulant system matrix (equation 31 or 32) is that the voxels of the cylindrical image should be rescaled according to the sum of all matrix coefficients of TORs contributing to each voxel. The rescaling step is performed only after the image reconstruction procedure since the application of the rescaling factors directly on the system matrix A would have broke the double block circulant structure of the matrix. When the image reconstruction method is based on a single block circulant matrix (equation 28 or 29), the rescaling step can be performed directly on the system matrix A in a precomputation step.

Several approaches are possible for reconstructing two-dimensional or three-dimensional images using the pseudo-inverse of the complex system matrix $\Delta^+$ or the SVD components obtained with a SVD procedure. As examples, three image reconstruction strategies are presented hereafter to illustrate how the method can be adapted to meet different requirements. It is to be understood that the non restrictive illustrative embodiment of the present invention is not limited to those examples.

Figure 18:
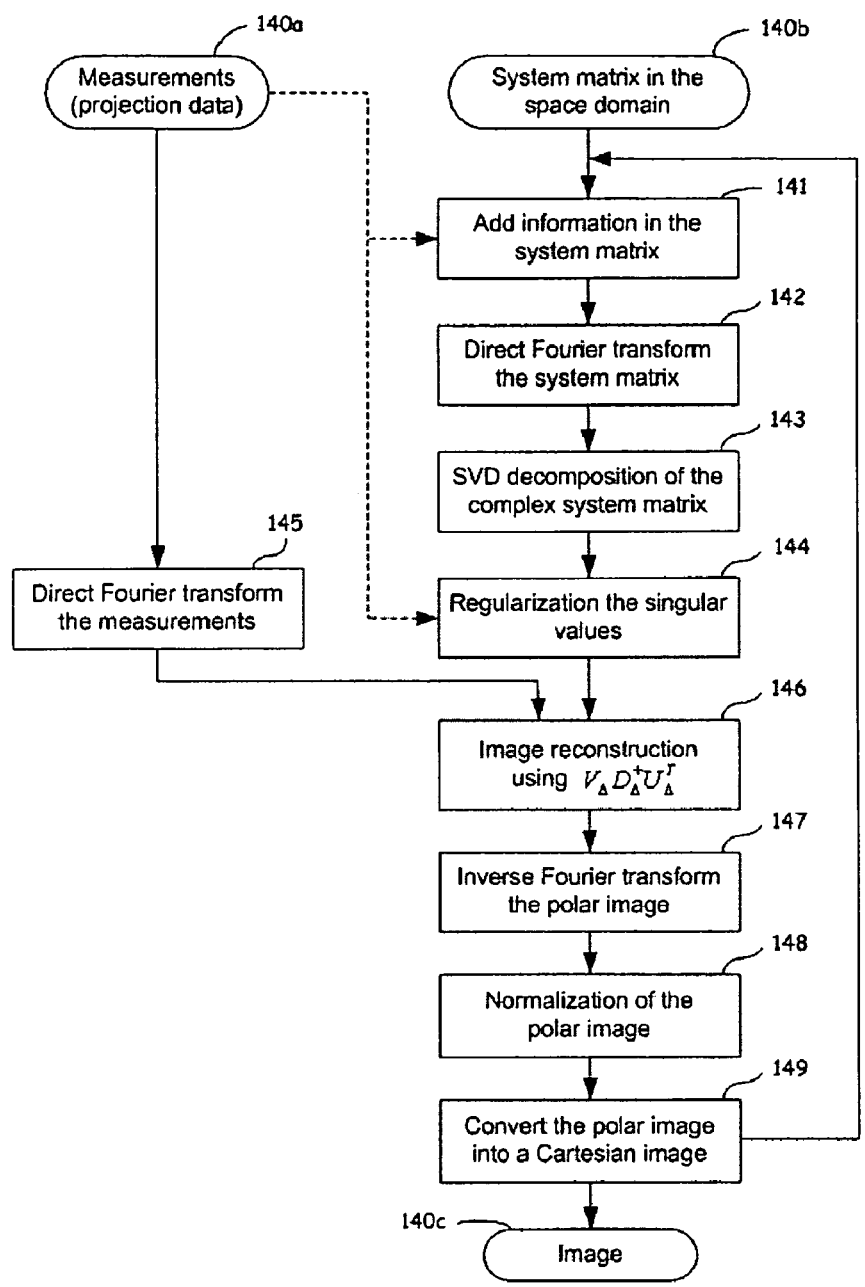
FIG. 18 is a block diagrammatic view of the main computation steps for reconstructing an image using a possible implementation of the direct image reconstruction method based on SVD decomposition of a block circulant system matrix.

The first image reconstruction strategy consists of performing the SVD decomposition of the system matrix A each time a new projection data set is to be reconstructed. A schematic view of the main computation steps of this method is illustrated in FIG. 18. This method allows the maximum flexibility since new information like an attenuation map, a scatter model or some other information which could be selected according to the characteristics of the projection data 140a, can be used to modify 141 the original system matrix A 140b to improve the quality of the reconstructed image 140c. The improved system matrix A 141 can then be Fourier transformed 142 to obtain a complex block-diagonal matrix $\Delta$ that is decomposed using an SVD algorithm 143. The singular value spectrum can then be regularized 144 according to the statistics of the projection data 140a and using some regularization methods (equations 24, 25, 26 and 27). The projection data 140a is Fourier transformed 145 and used with the regularized SVD components to reconstruct the polar or cylindrical image 146 that is further inverse Fourier transformed 147. Those steps correspond to equation 29 for a single block circulant system matrix or to equation 32 for a double block circulant system matrix. The last steps consist in normalizing the polar or cylindrical image 148 (if required) and in converting the polar or cylindrical image into a Cartesian image representation 149 (equation 10) to obtain an image 140c that can be shown on a conventional display.

Figure 19:
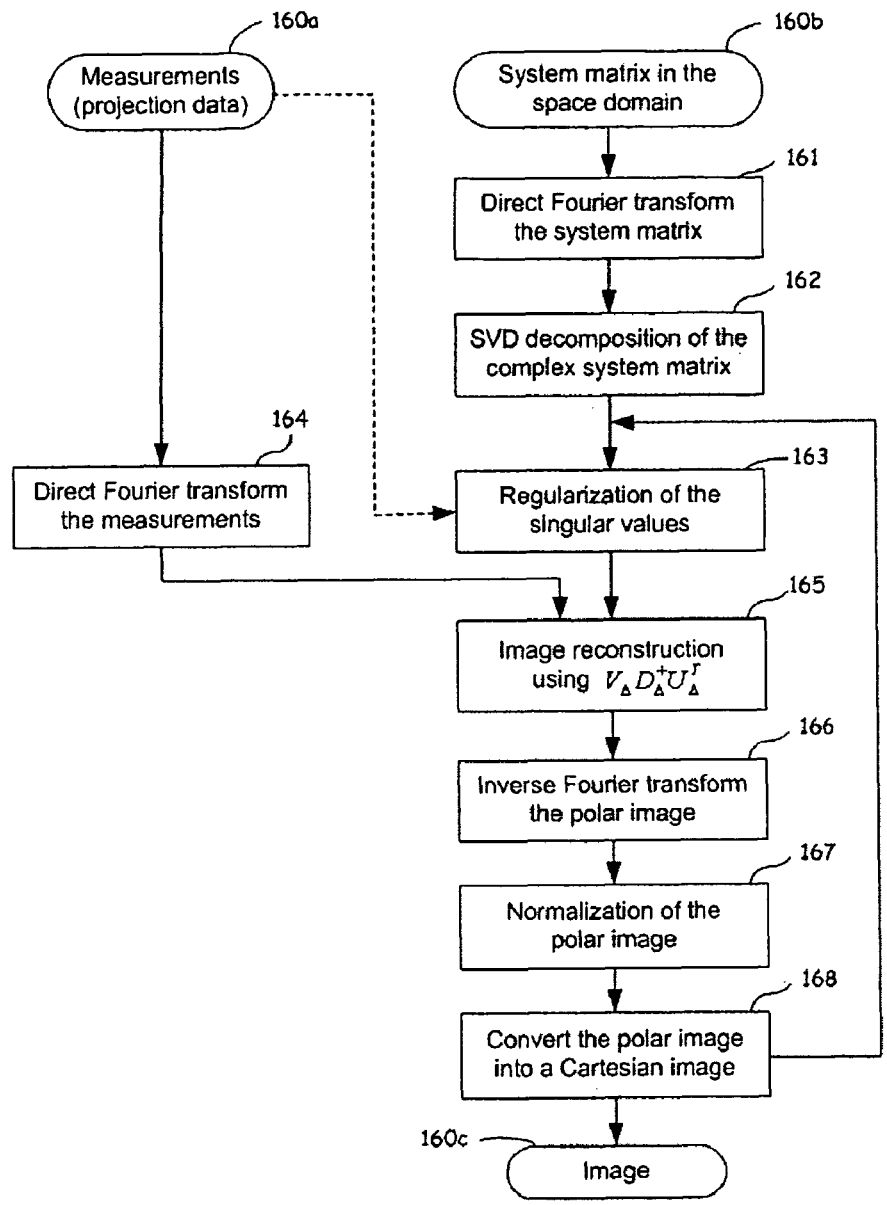
FIG. 19 is a block diagrammatic view of the main computation steps for reconstructing an image using another possible implementation of the direct image reconstruction method based on SVD decomposition of a block circulant system matrix.

The second image reconstruction strategy is very similar to the first one with the difference that the system matrix SVD decomposition step is performed only once in a precomputation step. This is illustrated in FIG. 19 where the direct Fourier transform 161 and the SVD decomposition 162 on the system matrix 160b are both performed in a precomputation step. Once the SVD components are obtained ($D_A$, $V_A$ and $U_A$), the original system matrix in the space domain 160b no longer needs to be stored in memory. By preserving the SVD components, one can still regularize the singular values contained in $D_A$ 163, with different methods (equations 24, 25, 26 and 27), to fit the statistics of the measurements and/or to control the trade-off between the noise amplification and the spatial resolution in the image. Moreover, when the regularization procedure consists in truncating the number of singular values, the computation of the image using the SVD components (equation 29 or 32) can lead to less operations than the use of the matrix pseudo-inverse $\Delta^+$ (equation 28 or 31) since one can use in the computation only the singular vectors in $V_A$ and $U_A$ that correspond to non-null singular values in $D_A$. The resulting algorithm is really fast since, each time new measurements are presented 160a, only the following steps are required: direct Fourier transforming the measurements 164, regularizing the singular values 163, reconstructing the image 165 using the SVD components (equation 29 or 32), inverse Fourier transforming the image 166, normalizing the polar image 167 and converting the polar or cylindrical image into a Cartesian image representation 168.

Figure 20:
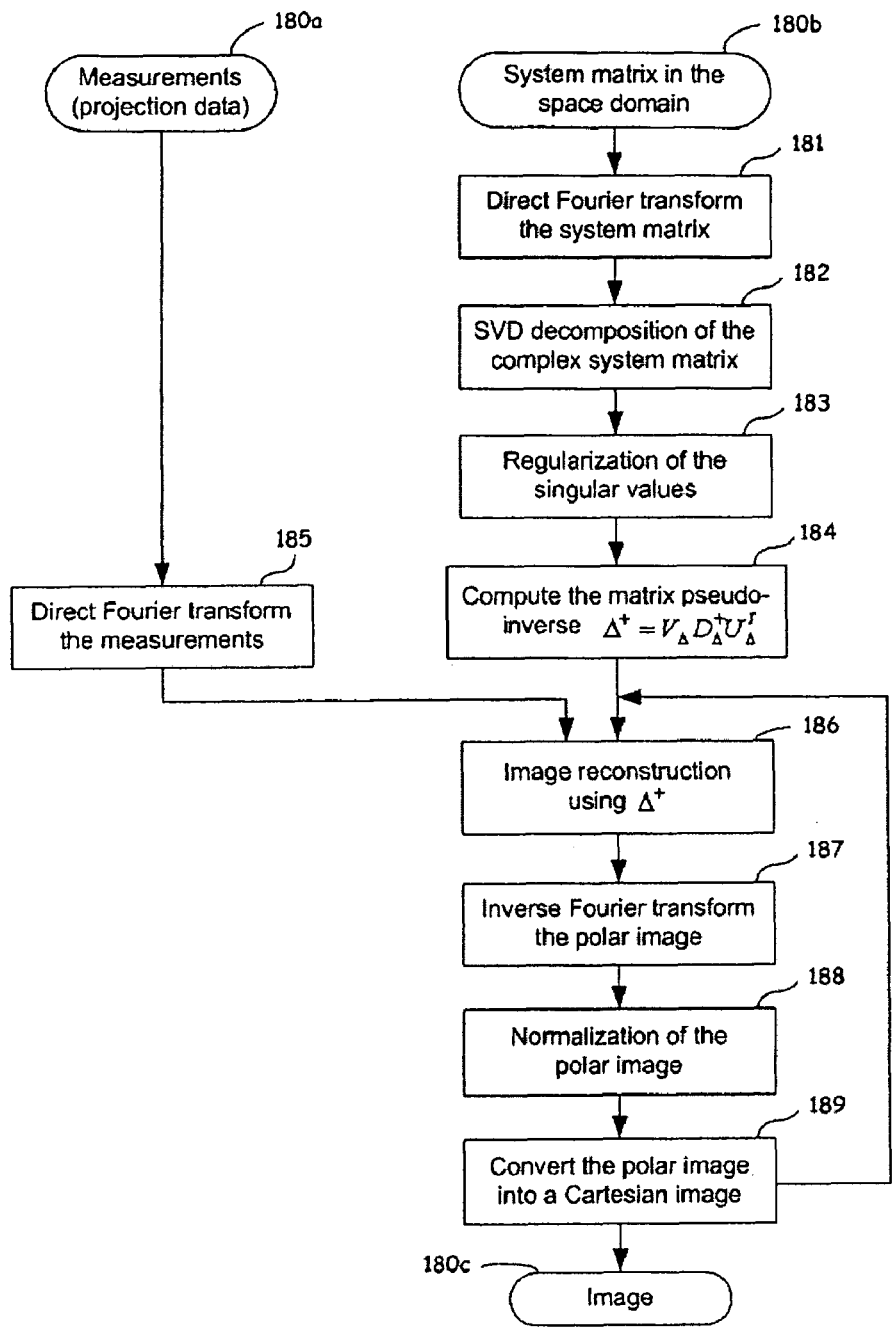
FIG. 20 is a block diagrammatic view of the main computation steps for reconstructing an image using another implementation of the direct image reconstruction method based on SVD decomposition of a block circulant system matrix.

The third image reconstruction strategy is based on a matrix-vector multiplication in the Fourier domain between the complex measurement vector and the complex pseudo-inverse system matrix $\Delta^+$. Referring to FIG. 20, the direct Fourier transform of the system matrix A 181, the SVD decomposition 182, the regularization of the singular value 183 and the computation of the complex pseudo-inverse matrix $\Delta^+$ 184 are all performed only once in a precomputation step. An advantage of reconstructing the image using the pseudo-inverse matrix $\Delta^+$ (equation 28 or 31) is that each group of $S_\theta$ symmetric pixels (equation 28) or of $(S_\phi \cdot S_\theta)$ symmetric voxels (equation 31) can be updated independently. This could lead to an image reconstruction procedure that can update sequentially and continuously different parts of the polar or cylindrical image. This could be particularly useful for real time visualization of 2D image slices reconstructed from 3D projection data since one can update only the voxels that are visible on the screen. An inconvenient of the method is that the regularization step 183 cannot be adapted to the properties of individual projection data since it is performed only once in a precomputation step.

Iterative Image Reconstructor

In the non-restrictive illustrative embodiment of the present invention, an iterative image reconstructor using a block circulant system matrix in the Fourier domain for computations in the forward and back projection steps is provided for two-dimensional and three-dimensional image reconstruction problems. The iterative image reconstructor can be decomposed in four main steps: 1) forward project an image estimate to obtain a measurement estimate, 2) compute a measurement correction vector using the measurement estimate and the measurements acquired with the apparatus, 3) back-project the measurement correction vector to obtain an image correction vector and 4) update the image estimate using the image correction vector. The non-restrictive illustrative embodiment of the present invention provides a general approach for accelerating the forward projection operation in step 1 and the back projection operation in step 3. The step 2 and the step 4 are more generally related to known procedures and will depend on the iterative solver and on some penalized or prior functions used in the iterative image reconstructor. However, the non-restrictive illustrative embodiment of the present invention comprises some modifications to the operation of updating the image estimate in step 4 in order to take into consideration the nature of the basis functions used in the polar or cylindrical image. The iterative solver used in the iterative image reconstructor can be of different kinds. For example, it can be a version of the Maximum Likelihood Expectation Minimization (MLEM) or a version of another algorithm, like for example, but not restricted to, the Ordered Subset Expectation Minimization (OSEM), the Rescaled Block Iterative (RBI), the Block Iterative Simultaneous MART algorithm (BI-SMART) or the Penalized Weighted Least-Squares (PWLS) algorithm.

To illustrate the different steps of the iterative image reconstructor, the theory will be presented for the well known Maximum Likelihood Expectation Minimization (MLEM) as an iterative solver. Shepp and Vardi were the first to propose the MLEM algorithm for tomographic image reconstruction problems [Shepp, "Maximum likelihood reconstruction for emission tomography", 1982]. The image update equation for each iteration of the EM algorithm proposed by Shepp and Vardi can be written as follows:

$$\bar{f}_j^{(k+1)} = \frac{\bar{f}_j^{(k)}}{\sum_{i=1}^{N} a_{i,j}} \cdot \sum_{i=1}^{N} \left( \frac{a_{i,j} y_i}{\sum_{b=0}^{B} a_{i,b} \bar{f}_b^{(k)}} \right) \text{ for } j = 1, \ldots, B \tag{33}$$

where $a_{i,j}$ are the coefficients of the system matrix A representing the probability that a disintegration coming from the $j^{th}$ voxel will be detected by the $i^{th}$ detector pair, $\bar{f}^{(k)}$ is a vector representing the source activity distribution in B source voxels at the $k^{th}$ iteration and y is a vector containing the N projections measured by the imaging system. For iterative methods, it is important to make a distinction between the vector y which contains the true measurement acquired by the imaging system from the vector $\bar{y}$ which contains an estimate of the measurement arising from the discretization of the image as state in equation 7.

The MLEM algorithm stated in equation 33 can be decomposed in the following steps:

(1) Forward project the image estimate $\bar{f}^{(k)}$ to obtain the measurement estimate $\bar{y}$:

$$\bar{y} = A\bar{f} \text{ or } \left\{ \bar{y}_i = \sum_{b=0}^{B} a_{ib} \bar{f}_b^{(k)} \text{ for } i = 1, \ldots, N \right\} \tag{34}$$

(2) Form the measurement correction vector $\epsilon$:

$$\varepsilon_i = \frac{y_i}{\bar{y}_i} \text{ for } i = 1, \ldots, N \tag{35}$$

(3) Back-project the measurement correction vector $\epsilon$ to obtain the image correction vector $\delta$:

$$\delta = A^T \varepsilon \text{ or } \left\{ \delta_j = \sum_{i=0}^{N} a_{ij} \varepsilon_i \text{ for } j = 1, \ldots, B \right\} \tag{36}$$

(4) Update the image estimate $\bar{f}^{(k+1)}$:

$$\bar{f}_j^{(k+1)} = \bar{f}_j^{(k)} \cdot \delta_j \text{ for } j = 1, \ldots, B \tag{37}$$

The system probability matrix A used in the forward projection (equation 34) and back projection (equation 35) steps may have a block circulant structure. Moreover, for three-dimensional problems the system probability matrix A can also be structured into a block circulant matrix where each blocks are themselves block circulant matrices. Methods for accelerating the forward and back projection computations will first be presented for two-dimensional problems and some additional considerations for three-dimensional problems will be explained thereafter.

For two-dimensional image reconstruction problems, it has been shown that the system matrix A based on a polar image can be reordered into a block circulant matrix having $S_\theta$ blocks of dimension n×m where n=$(N_\theta \cdot N_q)/S_\theta$ and m=$(B_\theta \cdot B_r)/S_\theta$. A block circulant matrix can be diagonalized using the Fourier transform:

$$A = (\mathfrak{S}_\theta \otimes I_n)^H \Delta (\mathfrak{S}_\theta \otimes I_m) \tag{38}$$

where $\mathfrak{S}_\theta$ is a normalized $S_\theta \times S_\theta$ discrete Fourier transform operator matrix with $w^k = \exp^{-j2\pi k/S_\theta}$:

$$\mathfrak{S}_\theta = \frac{1}{\sqrt{S_\theta}} \begin{bmatrix} 1 & 1 & 1 & \cdots & 1 \\ 1 & w^1 & w^2 & \cdots & w^{S_\theta - 1} \\ 1 & w^2 & w^4 & \cdots & w^{2(S_\theta - 1)} \\ \vdots & \vdots & \vdots & & \vdots \\ 1 & w^{S_\theta - 1} & w^{2(S_\theta - 1)} & \cdots & w^{(S_\theta - 1)(S_\theta - 1)} \end{bmatrix} \tag{39}$$

and $\Delta$ is a $S_\theta \cdot n \times S_\theta \cdot m$ complex block-diagonal matrix where each of the $S_\theta$ blocks are n×m:

$$\Delta = \begin{bmatrix} [\Delta_1] & & & [0] \\ & [\Delta_2] & & \\ & & \ddots & \\ [0] & & & [\Delta_{S_\theta}] \end{bmatrix} \tag{40}$$

and $1_n$ and $1_m$ are respectively n×n and m×m identity matrices, $\otimes$ is the Kronocker product and the subscript H is the Hermitian transpose (or conjugate transpose).

Using the complex block-diagonal matrix $\Delta$ in replacement to the original system matrix A for the forward and back projection steps can result in a reduction of the number of operations required. In theory, for a dense system matrix, the computational reduction would be proportional to the number of blocks $S_\theta$ in the block circulant matrix. However, in practice, the system matrix A is sparse (90%-99% of null values) and the matrix-vector operations performed in the forward and back projection steps of iterative image reconstruction methods are usually performed only on non-null coefficients of A to reduce the computation burden. When the system matrix A is diagonalized according to equation 38, a lot of null values become non-null during the Fourier transform operation. In fact, as soon as one matrix coefficient out of the $S_\theta$ symmetric coefficients (coefficients in one circulant submatrix) is non-null in the system matrix A, all the $S_\theta$ coefficients will become non-null after the Fourier transform operation. Nevertheless, the complex block-diagonal system matrix $\Delta$ will still preserve some null values. For example, symmetric TORs at a bin position that do not pass through the center of the polar image will never have contributions from pixels at the center of the image. Such a situation is illustrated in FIG. 12 where two symmetric TORs (111c and 112c) are at the same bin position (q=2) but at different angles ($\theta$=3, $\theta$=4). It can be seen that all the symmetric TORs at the bin position q=2 will never have contributions from the pixels at the innermost radius position r=0. Some other situations where all the $S_\theta$ symmetric coefficients are zeros may also arise for imaging system with less in-plane symmetries than the number of detectors in the ring.

In order to take advantage of the null values in the complex block-diagonal system matrix $\Delta$, it is advantageous to reorder the image vector $\bar{f}$ and the measurement vector y in such a way that symmetric voxels (and symmetric TORs) are stored in contiguous memory locations. This reordering can be performed using a permutation matrix $P_\theta$ which restructures the block circulant matrix A into (n·m) small circulant sub-matrices of dimension $S_\theta \times S_\theta$. Equation 38 then becomes:

$$A = P_\theta (I_n \otimes \mathfrak{S}_\theta)^T \Delta_p (I_m \otimes \mathfrak{S}_\theta) P_\theta \qquad (41)$$

where $\Delta_p$ is a $S_\theta \cdot n \times S_\theta \cdot m$ complex matrix made of (n·m) small diagonal matrices $D_{ij}$ of dimension $S_\theta \times S_\theta$:

$$\Delta_p = \begin{bmatrix} [D_{11}] & [D_{12}] & \dots & [D_{1m}] \\ [D_{21}] & [D_{22}] & \dots & [D_{2m}] \\ \vdots & \vdots & & \vdots \\ [D_{n1}] & [D_{n2}] & \dots & [D_{nm}] \end{bmatrix} \qquad (42)$$

The complex matrix $\Delta_p$ contains the same coefficients as the complex matrix $\Delta$ but ordered differently. Replacing the system matrix A with the complex system matrix $\Delta_p$ in the forward projection step, denoted by equation 34, and in back projection step, denoted by equation 36, will lead respectively to:

(1) Forward projection:

$$\bar{y} = P_\theta (I_n \otimes \mathfrak{S}_\theta)^H \Delta_p ((I_m \otimes \mathfrak{S}_\theta) P_\theta \bar{f}) \qquad (43)$$

(3) Back projection:

$$\delta = P_\theta (I_m \otimes \mathfrak{S}_\theta)^H \Delta_p^H ((I_n \otimes \mathfrak{S}_\theta) P_\theta \epsilon) \qquad (44)$$

One should notice that the same complex system matrix $\Delta_p$ can be used for the forward (equation 43) and back (equation 44) projection operations, the only requirement being that one must use the conjugate transpose of the matrix for the back projection step.

It is more advantageous to use the complex matrix $\Delta_p$ than the complex matrix $\Delta$ for accelerating the inner loop forward and back projection operations. A first advantage of using the matrix $\Delta_p$ over the matrix $\Delta$ comes from the reordering of the image vector $\bar{f}$ and the measurement vector y according to the permutation matrix $P_\theta$ which allows to regroup the symmetric data together. In the algorithm implementation of equations 43 and 44, the permutation matrix $P_\theta$ represents a reordering of the data that can be performed only once prior to entering in the iterative loop. All image vectors ($\bar{f}$ and $\delta$) and all measurement vectors (y, $\bar{y}$ and $\epsilon$) used in the inner loop (step 1 to step 4) of the iterative algorithm will therefore be reordered according to $P_\theta$, leading respectively to the ordering $\bar{f}_p = \{\bar{f}_{i,j} : i=1, \dots, m; j=1, \dots, S_\theta\}$ for image vectors and to the ordering $y_p = \{y_{i,j} : i=1, \dots, n; j=1, \dots, S_\theta\}$ for measurements vectors. The subscript p, denoting the permutation operation, was used to avoid confusion with the original data ordering. By regrouping all the $S_\theta$ symmetric pixels (or symmetric TORs) together, the direct (or inverse) Fourier transform can be performed more efficiently since the data are accessed on contiguous memory locations. A maximum acceleration is achieved by using Fast Fourier Transform (FFT) algorithms. Moreover, since the system matrix coefficients are real values, an order $S_\theta/2$ FFT transform can be used to transform a group of $S_\theta$ real values.

A second advantage of using the matrix $\Delta_p$ over the matrix $\Delta$ comes from the fact that the matrix $\Delta_p$ can be stored more efficiently in a sparse matrix format where only non-null diagonal matrices $D_{ij}$ are preserved in the system matrix. For example, null diagonal matrices can arise for i being a group of TORs at a bin position not passing through the FOV center and j being a group of pixels at a radius position near the FOV center. To access only the diagonal matrices $D_{ij}$ which have a non-null contribution to the $i^{th}$ group of symmetric TORs during the forward and back projection operations, an index vector is used to address the j=1, . . . , t; t≦m group of symmetric voxels reffered by the matrix $D_{ij}$. Storing the $\Delta_p$ matrix in sparse format allows to reduce the memory requirements and minimize the number of operations involved in the forward and back projection steps (equations 43 and 44).

Figure 21:
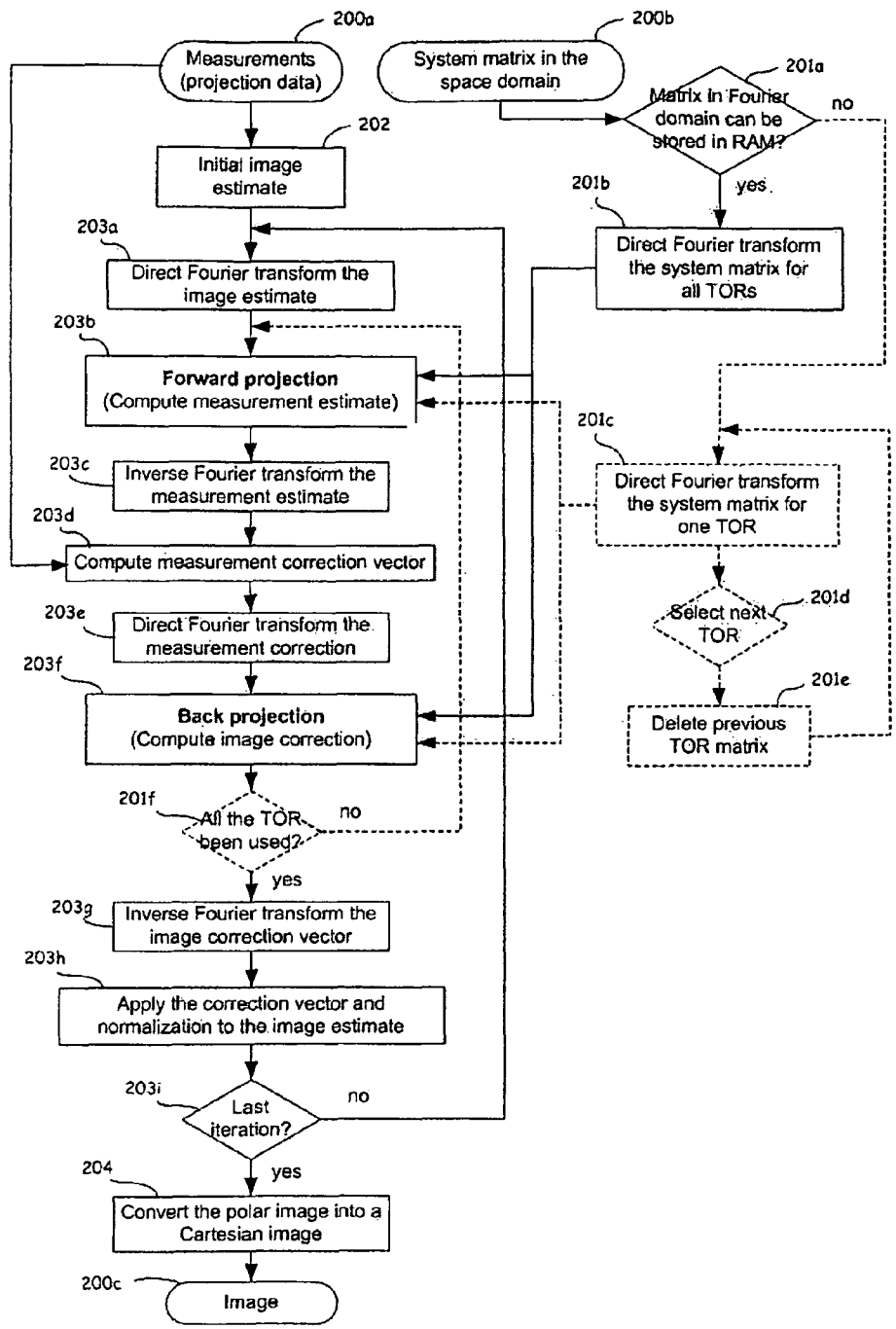
FIG. 21 is a block diagrammatic view of the main computation steps for reconstructing an image using possible implementations of an iterative image reconstruction method based on a block circulant system matrix.

A schematic view of the main computation steps of the iterative image reconstruction method of the non-restrictive illustrative embodiment of the present invention is shown in FIG. 21. In this method, projection data 200a and the block circulant system matrix 200b of a given imaging system are loaded before starting the computation. According to the availability of RAM memory in the processor where the algorithm is executed and depending on the size of the system matrix 200b, it may lead to a faster implementation to preserve the system matrix in the space domain and to Fourier transform the matrix coefficients of one or some group of symmetric TORs at a time 201c to feed the forward 203b and backward 203f projectors. The diagrams and links in dotted lines represent this option. Given that the block circulant system matrix in the Fourier domain (stored in sparse format) can fit in the RAM memory, it can save many operations to Fourier transform the complete system matrix 200b only once in a precomputation step 201b. Before entering in the iterative loop, an initial image estimate is selected 202. Usually the total number of counts in all projection data is distributed uniformly between all the image voxels. Other initial image estimates may also be selected. The iteration loop of the method can be decomposed in several steps (203a to 203f). The image estimate vector is transformed in the Fourier domain 203a to be forward projected 203b using the block circulant matrix. The result of the forward projection 203b is the measurement estimate vector that is inverse Fourier transformed 203c in order to compute the measurement correction vector 203d by some means which depend of the iterative solver used. The measurement correction vector is then Fourier transformed 203e to be back projected 203f in order to compute the image correction vector. An inner loop 201f used to perform the forward and back projections of one or some group of symmetric TORs at a time is required only when the system matrix is transformed in the Fourier domain on one or some groups of symmetric LORs at a time 201c. Nevertheless, the inner loop 201f can also be used when the complete system matrix is Fourier transformed 201b. Once all TORs have been used in the forward and back projection steps, the obtained image correction vector is inverse Fourier transformed 203g to be used for the update of the current image estimate 203h. The image estimate should also be normalized according to the sum of TOR matrix coefficients which contribute to every voxel (first denominator in equation 33). This is the last step of one iteration loop. If more iterations are required, the new image estimate is used in the next iteration loop and is therefore Fourier transformed in step 203a. If no more iterations are required, the polar or cylindrical image is converted 204 into a square pixel Cartesian image 200c using a conversion table $T_{pc}$ (equation 10). The final image 200c can be displayed on screen or saved in some memory storage.

According to some aspects, the step of correcting the image estimate 203h involves some modifications when a polar or cylindrical image representation is used. For statistical reasons, the pixel area (or voxel volume) of the image should be the same when performing the update of the pixel value estimate in the iterative loop. Pixels size disparities are reduced by the use of a polar or cylindrical image representation having more pixels at radius position farther from the FOV center. An example of such a polar or cylindrical image is shown in FIG. 11. However, for a system having an important number of in-plane symmetries $N_\theta$, the innermost pixel area can still be significantly smaller than the area of other pixels in the image. Hebert [Hebert, Fast MLE for SPECT using an intermediate polar representation and a stopping criterion] proposed to convert the polar image into a Cartesian image before the correction is applied to the image estimate 203h and then to convert the image back into a polar image representation. A first disadvantage of this method is the loss of spatial resolution (or blurring effect) caused by going back and forth into two different image representations having pixels with different shape, size and position. To reduce the pixel area disparities between innermost pixels and other pixels of the image, we proposed to combine the innermost pixel estimate values of two, three or more pixels (or voxels) together before the image correction is applied. This is equivalent to double, triple or multiply by some other factors the area (or volume) of the innermost pixels (or voxels). For example, referring to FIG. 11, before updating the innermost pixel image estimates at the radius position $r_0$, the pixel image estimates at the angle position $\theta_0$ and $\theta_1$ could be summed together to form a new pixel image estimate having twice the initial pixel area. The same operation is applied to the image correction vector so that the correction value for pixel ($r_0$, $\theta_0$) and pixel ($r_0$, $\theta_1$) are summed together before the correction is applied to the image estimate. Both pixels ($r_0$, $\theta_0$) and ($r_0$, $\theta_1$) will then be set to the same image estimate value. Alternatively, given that the pixel area disparities in the polar or cylindrical image is in an acceptable range, it can lead to a valid and faster implementation to use the original polar or cylindrical image representation for the image estimate correction operation 203h.

Hebert [Hebert, Fast MLE for SPECT using an intermediate polar representation and a stopping criterion] proposed a method for accelerating the forward and the back projection operations for two-dimensional SPECT image reconstruction problems through the use of a block circulant probability matrix in the Fourier domain. The method was proposed for a SPECT rotating detector gantry and was based on a polar image representation having the same number of pixels at each radius position. This configuration of the image lead to important size disparities between the innermost and the outermost pixels leading to lost of spatial resolution on outermost region of the image. The spatial resolution can be recovered by using twice the number of angles in the image but at the cost of doubling the computation requirement. Moreover, all the coefficients of the block circulant system matrix were used in the matrix-vector computations leading to sub-optimal computational speed and to a rapid decrease of performance as the number of in-plane symmetries in a camera is reduced. The decrease of performance and the limitations imposed by the polar image representation used by Hebert makes this image reconstruction method effective only for imaging system having perfect (or near perfect) in-plane symmetries between all the detectors within the ring.

According to some aspects of the non-restrictive illustrative embodiment of the present invention, two main contributions are proposed to overcome the limitations of the method proposed by Hebert for two-dimensional image reconstruction problems. The new iterative image reconstruction method of the non-restrictive illustrative embodiment of the present invention leads to gain of speed in the forward and back projection operations even for imaging system with few symmetries. The first main contribution is the demonstration that a polar image having an unequal number of pixels at different radius position can also be structured into a block circulant probability matrix and be used to accelerate computation in the forward and back projection steps. Such a polar image definition were used in other works like in [Kaufman, Implementing and accelerating the EM algorithm for positron emission tomography] and more recently in [Mora, Polar pixels for high resolution small animal PET] but the aim in those works was only to reduce the system matrix size. In other words, they did not restructure the system matrix into a block circulant matrix and they did not used the Fourier transform to accelerate the computation. Another contribution of the non-restrictive illustrative embodiment of the present invention is the restructuration of the block circulant system matrix in the Fourier domain into a sparse matrix format. By using a sparse matrix format, the size of the system matrix and the number of operations can be reduced significantly for camera with perfect symmetries and even more for camera having less symmetries than the number of detectors within the ring.

Another contribution of the non-restrictive illustrative embodiment of the present invention is to extend the iterative image reconstruction method based on block circulant matrix to three-dimensional image reconstruction problems and to demonstrate that further matrix size reduction and computational saving is possible through the use of the axial symmetries between the scanner projection planes. Accordingly, it was shown in FIG. 14 that a block circulant matrix where each block are themselves block circulant matrices can be obtained for three-dimensional image reconstruction problems. In the non-restrictive illustrative embodiment of the present invention, two different methods are provided for accelerating the forward and back projection operations using block circulant matrix in three-dimensional image reconstruction problems. Those methods are explained hereafter.

The first method consists of performing the Fourier transform only on the circulant sub-matrices made from in-plane symmetries of the camera. In this case, the system matrix A can be structured in a simple block circulant matrix. The forward and back projection steps are then performed independently on each projection planes of a 3D camera using the equations 43 and 44 with $\Delta_p^{(i,j)}$ being the block circulant matrix for the $i^{th}$ projection plane and for the $j^{th}$ image slice and with n=($N_\theta \cdot N_q$)/$S_\theta$ and m=($B_\theta \cdot B_r$)/$S_\theta$ as for two-dimensional image reconstruction problems. Accordingly, the forward and back projection steps of the iterative algorithm can be replaced by:

(1) Forward projection:

$$\bar{y}^{(i)} = \sum_{j=1}^{(B_{\phi z})} \left[ P_\theta (I_n \otimes \mathcal{J}_\theta)^H \Delta_p^{(i,j)} \left( (I_m \otimes \mathcal{J}_\theta) P_\theta \bar{f}^{(j)} \right) \right] \quad (45)$$

for $i = 1, \ldots, N_{\phi p}$ (3) Back projection:

$$\delta^{(j)} = \sum_{i=1}^{N_{\phi P}} \left[ P_\theta (I_m \otimes \mathcal{J}_\theta)^H (\Delta_p^{(i,j)})^H ((I_n \otimes \mathcal{J}_\theta) P_\theta \varepsilon^{(i)}) \right] \quad (46)$$

for $j = 1, \ldots, B_{\phi z}$ where $\bar{y}^{(i)}$ and $\epsilon^{(i)}$ represent respectively the measurement estimate and measurement correction vectors for the $i^{th}$ projection plane, $N_{\phi p}=(N_\phi \cdot N_p - \alpha)$ is the total number of projection planes measured by the apparatus, $\bar{f}^{(j)}$ and $\delta^{(j)}$ represent respectively the image estimate and image correction vectors for the $j^{th}$ 2D image slice and $B_{\phi z}=(B_\phi \cdot B_z)$ is the number of 2D image slices in the 3D image. Moreover, by using the axial translational and mirror symmetries in the imaging system, it is possible to reduce the number of system sub-matrices $\Delta_p^{(ij)}$ that need to be computed and stored in memory. Instead of storing $N_{\phi p} \cdot B_{\phi z}$ sub-matrices, it is possible to store only $N_p \cdot B_{\phi z}$ sub-matrices, where $N_p$ is the number of non-symmetric projection planes. Using the 4-ring scanner example illustrated in FIG. 4, the use of the axial symmetries would allow to reduce the number of sub-matrices $\Delta_p^{(ij)}$ by a factor of four since $N_{\phi p}=16$ and $N_p=4$ for this scanner configuration. However, special care has to be taken when using the mirror symmetries since the ordering of the 2D image slices should be inverted when the mirrored projection plane is used in the forward or in the back projection operations. Referring to FIG. 21, the use of axial symmetries in the system also allows to reduce the overhead of performing the direct and inverse Fourier transforms on the measurement vectors (steps 203c and 203e) and on the image vectors (steps 203a and 203g) compared to the time required to perform the forward (step 203b) and back (step 203f) projection operations since the result of the Fourier transform of one group of in-plane symmetric voxels (or TORs) is reused by all axial symmetric projection planes (or 2D image slices).

The second strategy for accelerating the forward and back projection operations for three-dimensional image reconstruction problems consists of performing two successive Fourier transform operations on the double block circulant matrix in order to take advantage of both the in-plane and the axial symmetries of the apparatus. In contrast to the first strategy, the second strategy restructures the system matrix A into a double block circulant matrix which requires some unmeasured projection planes to be added in the system matrix equations. The obtention of the double block circulant matrix was discussed previously and an example was presented in FIG. 14. Accordingly, the double block circulant system matrix A can be replaced by the following relation:

$$A = (\Im_\theta \otimes I_{(n \cdot \phi)})^H P_\phi (\Im_\phi \otimes I_{(n \cdot \theta)})^H \Delta (\Im_\phi \otimes I_{(m \cdot \theta)})$$
$$P_\phi (\Im_\theta \otimes I_{(m \cdot \phi)}) \tag{47}$$

or equivalently by $$A = P_\theta (I_{(n \cdot \phi)} \otimes \Im_\theta)^H P_\phi (I_{(n \cdot \theta)} \otimes \Im_\phi)^H \Delta_p$$
$$(I_{(m \cdot \theta)} \otimes \Im_\phi) P_\phi (I_{(m \cdot \phi)} \otimes \Im_\theta) P_\theta \tag{48}$$

where $\Im_\phi$ and $\Im_\theta$ are respectively $S_\phi \times S_\phi$ and $S_\theta \times S_\theta$ discrete Fourier transform operators, $I_{(n \cdot \phi)}$, $I_{(n \cdot \theta)}$, $I_{(m \cdot \phi)}$ and $I_{(m \cdot \theta)}$ are respectively $n \cdot S_\phi \times n \cdot S_\phi$, $n \cdot S_\theta \times n \cdot S_\theta$, $m \cdot S_\phi \times m \cdot S_\phi$ and $m \cdot S_\theta \times m \cdot S_\theta$ identity matrices, $P_\phi$ and $P_\theta$ are permutation matrices which reorder the data so that respectively the Fourier operator $\Im_\phi$ and $\Im_\theta$ could be performed. In equation 47, $\Delta$ is a $S_\phi \cdot S_\theta \cdot n \times S_\phi \cdot S_\theta \cdot m$ complex block-diagonal matrix with a structure similar to the matrix in equation 40 but having $(S_\phi \cdot S_\theta)$ blocks of dimension n×m. In equation 48, $\Delta_p$ is a $S_\phi \cdot S_\theta \cdot n \times S_\phi \cdot S_\theta \cdot m$ complex matrix with a structure similar to the matrix in equation 42 but having (n·m) small diagonal matrices $D_{ij}$ of dimension $S_\phi \cdot S_\theta \times S_\phi \cdot S_\theta$. Finally, n and m will depend respectively on the geometry of the apparatus and of the image and will be set according to $n = (N_\theta \cdot N_q \cdot N_\phi \cdot N_p)/S_\phi \cdot S_\theta)$ and $m = B/(S_\phi \cdot S_\theta)$.

It is important to add some precisions concerning the permutation matrices $P_\phi$ and $P_\theta$. A first concern is that the matrix $P_\phi$ in equations 47 and 48 will not have the same structure due to a different ordering of the Fourier operator $\Im_\phi$. The implementation of equation 48 usually leads to a faster algorithm than the implementation of equation 47. This is in part due to the more appropriate data ordering obtained with the permutation matrices $P_\phi$ and $P_\theta$. Referring to equation 48, the permutation matrix $P_\theta$ first reorder the data into (m·$\phi$) circulant sub-matrices of size $S_\theta \times S_\theta$ so that the Fourier operator $\Im_\theta$ can be applied on contiguous memory locations. The result of the first Fourier transform is then reordered into (m·$\theta$) circulant sub-matrices to apply the Fourier operator $\Im_\phi$. Another aspect that make the equation 48 more advantageous than the equation 47 is that the complex matrix $\Delta_p$ can be stored more efficiently in a sparse matrix format than the complex matrix $\Delta$. However, the reordering of the operations in equation 47 and 48 may lead to other possible implementations and all those different implementations are within the scope of the present invention.

Using for example the double block circulant system matrix restructuration of equation 47, the forward and back projection steps of the said iterative algorithm can be replaced by:

(1) Forward projection:

$$\bar{y} = P_\theta (I_{(n \cdot \phi)} \otimes \Im_\theta)^H P_\phi (I_{(n \cdot \theta)} \otimes \Im_\phi)^H \Delta_p$$
$$((I_{(m \cdot \theta)} \otimes \Im_\phi) P_\phi (I_{(m \cdot \phi)} \otimes \Im_\theta) P_\theta \bar{f}) \tag{49}$$

(3) Back projection:

$$\delta = P_\theta (I_{(m \cdot \phi)} \otimes \Im_\theta)^H P_\phi (I_{(m \cdot \theta)} \otimes \Im_\phi)^H \Delta_p$$
$$((I_{(n \cdot \theta)} \otimes \Im_\phi) P_\phi (I_{(n \cdot \phi)} \otimes \Im_\theta) P_\theta \epsilon) \tag{50}$$

In the implementation of equations 49 and 50, the permutation matrix $P_\theta$ can be performed only once prior entering in the iterative loop. All image vectors ($\bar{f}$ and $\delta$) and all measurement vectors (y, $\bar{y}$ and $\epsilon$) used in the inner loop (step 1 to step 4) of the iterative algorithm can therefore be reordered according to $\bar{f}_p = \{\bar{f}_{i,j,k} : i=1, \ldots, m; j=1, \ldots, S_\phi, k=1, \ldots, S_\theta\}$ for image vectors and to $y_p = \{y_{i,j,k} : i=1, \ldots, n; j=1, \ldots, S_\phi, k=1, \ldots, S_\theta\}$ for measurements vectors. After the first Fourier transform $\Im_\theta$, the permutation matrix $P_\phi$ regroup all data having axial symmetries together for the second Fourier transform $\Im_\phi$, leading to $\bar{f}_p = \{\bar{f}_{i,j,k} : i=1, \ldots, m; j=1, \ldots, S_\theta, k=1, \ldots, S_\phi\}$ for the image vectors and to $y_p = \{y_{i,j,k} : i=1, \ldots, n; j=1, \ldots, S_\theta, k=1, \ldots, S_\phi\}$ for the measurement vectors.

The three-dimensional iterative image reconstruction methods of the non restrictive illustrative embodiment of the present invention can be decomposed in several computational steps that are similar to the ones required for two-dimensional problems. Referring to FIG. 21, the forward 203b and back projection operations 203f are replaced respectively by equations 45 and 46 if the single block circulant matrix acceleration strategy is used or by equations 49 and 50 if the double block circulant matrix acceleration strategy is used. The second strategy requires however a special handling of the unmeasured projection planes during the measurement correction operation 203d. As mentioned previously, some unmeasured projection planes were inserted in the system matrix equation to obtain the double block circulant system matrix structure. Those unmeasured projection planes will not affect the result given that they are ignored during the measurement correction operation 203d and that they are set to zero in the measurement correction vector $\epsilon$ so that they do not affect the result of the back projection operation 203f.

Another particularity of three-dimensional image reconstruction problems compared to two-dimensional problems is the important size increase of the system matrix A and consequently of the complex system matrix $\Delta_p$. Since the complex system matrix $\Delta_p$ may not fit completely in RAM memory of a given workstation for some 3D image reconstruction problems, it could be more advantageous to store only the system matrix A in the space domain and to Fourier transform only the matrix coefficients of one or some groups of symmetric TORs at a time. This option 201a is illustrated in FIG. 21. When a double block circulant system matrix is used, it is possible to perform only the first Fourier transform in a precomputation step to limit the memory requirement and to perform the second Fourier operation repeatedly at each iteration loop to feed the forward and back projector. If the system matrix A in the space domain is really huge, one can also decide to compute the system matrix coefficients on-the-flag and thus to Fourier transform the matrix coefficients of one or some groups of symmetric TORs at a time. Moreover, it is to be understood that all those methods can also be used for the other cases where the system matrix ordering is modified so that the forward and back projection operations used the matrix coefficients of one or some groups of symmetric voxels at a time.

In the non-restrictive illustrative embodiment of the present invention, the choice of performing the forward and back projection operations according to the first implementation strategy (equations 45 and 46) or according to the double block circulant matrix implementation strategy (equations 49 and 50) will depend on the ratio of null values in the system matrix A and on the number of symmetries in the imaging system. The architecture of the processor or of any computation unit where the image reconstruction algorithm is implemented may also influence the choice of strategy. An advantage of using only one Fourier transform operator instead of two is that the complex system matrix $\Delta_p$ will preserve more null values in $\Delta_p$ and therefore will require less memory to be stored. The inclusion of unmeasured projection planes in the system matrix for the double block circulant matrix strategy also increases the size of $\Delta_p$. Moreover, the single block circulant matrix strategy involves less operations for the direct and inverse Fourier transform since only one Fourier operator is used ($\Im_\theta$) compared to two Fourier operators ($\Im_\phi$ and $\Im_\theta$) for the double block circulant matrix strategy. However, once an image or a measurement vector has been Fourier transformed, the double block circulant matrix strategy is the one that minimizes the number of complex matrix-vector operations between the complex matrix $\Delta_p$ and the image or measurement vectors. Making the sum of advantages and disadvantage of both methods, the double block circulant matrix strategy can lead to better performance for imaging system with many axial symmetries and when the system matrix A is less sparse. For example, in PET, the system matrix can become less sparse if scatter coincidences are also modeled in the system matrix.

Another method that can make the double block circulant matrix strategy more advantageous than the single block circulant one is the increase of the number of axial symmetries in the system by performing successive acquisition taken at different bed positions along the z-axis. Oversampling along the z-axis is possible by performing bed displacement that are half, a quarter or some other factors of the detector height. Different methods can then be used to recombine the acquisition frames taken at different bed positions as shown in FIG. 16 and FIG. 17. Merging data coming from different acquisition frames is very favorable for iterative image reconstructions since it increases the statistics collected at each projection plane. Moreover, the method of the non restrictive illustrative embodiment of the present invention will reconstruct really rapidly those extended projection data set by using the axial symmetries.

Another kind of iterative solver can be selected in replacement to the MLEM algorithm. For example, the use of a block iterative algorithm, like the OSEM algorithm, can allow to increase even more the computational speed of the iterative image reconstruction methods. The adaptation to other iterative solvers is straightforward. Block iterative methods consist in dividing the measurement vector into different subsets that are used one after the other in the forward and back projection steps to update the image estimate vector. The subsets can also be made from groups of voxels. One iteration loop is completed when all the subsets have been used in the computation to update the image estimate. The only constraint when using a block iterative solver is that the number of data in a subset must be an integer factor of the number of blocks in the block circulant system matrix used in the forward and back projection steps. For two-dimensional image reconstruction problems and three-dimensional problems using one Fourier transform operators ($\Im_\theta$), the number of data in a subset $M_s$ is a factor of the number of in-plane symmetries in the camera, leading to $M_s = k \cdot S_\theta$ where k is an integer. For three-dimensional image reconstruction problems using two Fourier transform operators ($\Im_\phi$ and $\Im_\theta$) to accelerate the forward and back projection steps, the number of data in a subset $M_s$ is a factor of the number of in-plane and axial symmetries, leading to $M_s = k \cdot S_\phi \cdot S_\theta$ where k is an integer. Referring to FIG. 8, when measurement subsets (or image subsets) are used, the steps (203a, 203b, 203c, 203d, 203e, 203f, 201f, 203g, and 203h) in the iterative loop are performed using only one subset at a time. An inner loop inside the iterative loop is then used to loop through all the N/$M_s$ measurement subsets (or the B/$M_s$ image subsets).

Although the present invention has been described in the foregoing description in relation to a non-restrictive illustrative embodiment thereof, this embodiment can be modified without departing from the spirit and nature of the present invention.

REFERENCES

[Barber, Image reconstruction, "European patent specification", 1992]
Image reconstruction, Barber, David, Charles, EP0670067B1
[Buonocore, A natural pixel decomposition for two-dimensional image reconstruction, 1980]
BUONOCORE, M. H., BRODY, W. R. and MACOVSKI, A. (1981) *A natural pixel decomposition for two-dimensional image reconstruction*, IEEE Trans. Biomed. Eng., vol. 28, p. 69-78.
[Llacer, Tomographic image reconstruction by eigenvector decomposition: Its limitations and areas of application, 1982]
LLACER, J. (1982) *Tomographic image reconstruction by eigenvector decomposition: Its limitations and areas of applicability*, IEEE Transactions on Medical Imaging, vol. MI-1, no. 1, p. 34-42.
[Baker, "Generalized approach to inverse problems in tomography: Image reconstruction for spatially variant systems using natural pixels", 1992]
BAKER, J. R., BUDINGER, T. F. and HUESMAN, R. H. (1992) Generalized approach to inverse problems in tomography: Image reconstruction for spatially variant systems using natural pixels, Critical Review Biomedical Engineering, vol. 20, p. 47-71.
[Shim, "SVD Pseudoinversion image reconstruction, 1981]
SHIM, Y. S. and CHO, Z. H. (1981) *SVD pseudoinversion image reconstruction*, IEEE Trans. ASSP, vol. 29, p. 904-909.
[Vandenberghe, "Reconstruction of 2D PET data with Monte Carlo generated natural pixels, 2006]
VANDENGERGHE, S., STAELENS, S., BYRNES, C. L., SOARES, E. J., LEMAHIEU, I. and GLICK, S. (2006) *Reconstruction of 2D PET data with Monte Carlo generated system matrix for generalized natural pixels*, Physics in Medicine Biology, vol. 51, p. 3105-3125.

[Selivanov, "Fast PET image reconstruction based on SVD decomposition of the system matrix, 2001]
SELIVANOV, V. V. and LECOMTE, R. (June 2001) *Fast PET image reconstruction based on SVD decomposition of the system matrix*, IEEE Trans. Nucl. Sci., vol. 48, no. 3, p. 761-767.
[Hudson, "Accelerated image reconstruction using ordered subsets of projection data", 1994]
HUDSON, H. M. and LARKIN, R. S. (December 1994) *Accelerated image reconstruction using ordered subsets of projection data*, IEEE Trans. Med. Imaging, vol. 13, no. 4, p. 601-609.
[Shepp, "Maximum likelihood reconstruction for emission tomography", 1982]
SHEPP, L. A. and VARDI, Y. (October 1982) *Maximum likelihood reconstruction for emission tomography*, IEEE Trans. on Medical Imaging, vol. MI-1, no. 2, p. 113-122.
[Kearfott, K. J., "Comment: Practical considerations;", Journal of the American Statistical Association, 1985]
KEARFOTT, K. J. (March 1985) *Comment: Practical considerations*, Journal of the American Statistical Association, p. 26-28.
[Kaufman, Implementing and accelerating the EM algorithm for positron emission tomography, 1987]
KAUFMAN, L. (March 1987) *Implementing and accelerating the EM algorithm for positron emission tomography*, IEEE Trans. Med. Imaging, vol. MI-6, no. 1, p. 37-51.
[Hebert, Fast MLE for SPECT using an intermediate polar representation and a stopping criterion, 1988]
HEBERT, T., LEAHY, R. and SINGH, M. (February 1988) *Fast MLE for SPECT using an intermediate polar representation and a stopping criterion*, IEEE Trans. Nucl. Sci., vol. 35, no. 1, p. 615-619.
[Mora, Polar pixels for high resolution small animal PET, 2006]
MORA, C. et RAFECAS, M. (October 2006), *Polar pixels for high resolution small PET*, Conference Record 2006 IEEE NSS/MIC, San Diego, Calif.

What is claimed is:

1. An imaging system, comprising:
a plurality of detectors each so configured as to generate a signal which is used to make measurements of an object along a respective projection;
a translating table so configured as to receive an object thereon and operable to translate in relation to the plurality of detectors;
a signal processor so coupled to the plurality of detectors as to receive and process the signals generated by the detectors; the signal processor being so configured as to extract relevant information in accordance with an imaging modality of the imaging system;
an acquisition system so coupled to the signal processor as to collect the information extracted by the signal processor and information about an actual position of the translating table; the acquisition system being so configured as to produce projection data; and
an image reconstructor so coupled to the acquisition system as to receive the projection data and reconstruct an image in response to the projection data; the image reconstructor being so configured as to reconstruct the image by:
choosing a polar or cylindrical image definition which comprises a polar or cylindrical grid representation and basis functions defined over the polar or cylindrical grid in order to preserve symmetries between lines of response of the imaging system;
computing a probability matrix that relates each of the projection data to each basis function of the polar or cylindrical grid representation;
restructuring the probability matrix into a block circulant matrix;
computing a polar or cylindrical image of the object using the block circulant matrix in Fourier domain; and
converting the computed polar or cylindrical image into a Cartesian image representation to thereby obtain a reconstructed image of the object.

2. The system of claim 1, wherein the image reconstructor reconstructs the image of the object by using a matrix-vector operation in the Fourier domain between an inverted block circulant matrix in the Fourier domain and the projection data in the Fourier domain, wherein the inverted block circulant matrix is obtained by pseudo-inverting the block circulant matrix using singular value decomposition.

3. The system of claim 1, wherein the image reconstructor is reconstructing the image of the object using an iterative solver based on the block circulant matrix; the iterative solver comprising the steps of:
making an initial image estimate;
forward projecting in the Fourier domain the image estimate with the probability matrix to obtain an estimate of the projection data;
computing a projection correction vector using the estimate and a true measurement along the projection data;
back projecting in the Fourier domain the projection correction vector with a transposed of the system probability matrix to obtain an image correction vector;
modifying the image estimate using the image correction vector; and iterating back to the step of forward projecting until the image estimate reaches convergence.

4. The system of claim 1, wherein the acquisition system collects projection data along a two-dimensional slice of the object and wherein the polar image is a two-dimensional image.

5. The system of claim 1, wherein the acquisition system is collecting projection data along a three-dimensional volume of the object and wherein the cylindrical image is a three-dimensional image.

6. The system of claim 1, wherein the plurality of detectors comprises at least one ring of detectors.

7. The system of claim 1, wherein the plurality of detectors comprises at least one gantry of detectors that is rotatable around the object.

8. The system of claim 1, wherein the imaging system comprises a positron emission tomography (PET) imaging system.

9. The system of claim 1, wherein the imaging system is selected from the group consisting of a computed tomography (CT) system, an X-ray imaging system, a single photon emission computed tomography (SPECT) system and a ultrasound system.

10. The system of claim 1, wherein the translating table comprises a bed that supports the object being measured and that can be translated along an axial direction of the imaging system and wherein a bed position is retrieved by the acquisition system and is included in the projection data.

11. The system of claim 1, wherein the imaging system provides for a maximized number of in plane and axial symmetries between the lines of response of the imaging system.

12. An iterative image reconstruction method to be used in connection with an imaging system that generates projection data, the reconstruction method comprising the steps of:
  (a) collecting the projection data generated by the imaging system;
  (b) choosing a polar or cylindrical image definition which comprises a polar or cylindrical grid representation and a number of basis functions positioned according to the polar or cylindrical grid so that the number of basis functions at different radius positions of the polar or cylindrical image grid is a factor of a number of in-plane symmetries between lines of response along which the projection data are measured by the imaging system;
  (c) obtaining a probability matrix that relates each of the projection data to each basis function of the polar image definition;
  (d) restructuring the probability matrix into a block circulant matrix and converting the probability matrix in Fourier domain to accelerate matrix-vector operations using the probability matrix;
  (e) storing and arranging in a suitable form the projection data into a measurement data vector;
  (f) providing an initial polar or cylindrical image estimate;
  (g) for each iteration; recalculating the polar or cylindrical image estimate according to an iterative solver that is based on forward and back projection operations with the probability matrix in the Fourier domain; and
  (h) converting the polar or cylindrical image estimate into a Cartesian image representation to thereby obtain a reconstructed image.

13. A method as recited in claim 12, wherein obtaining the system probability matrix comprises computing the probability matrix in relation to physical aspects of the imaging system, a geometry, shape and properties of detectors in the imaging system, the polar or cylindrical grid representation and the basis functions used in the polar or cylindrical grip representation.

14. An iterative image reconstruction method to be used in connection with an imaging system that generates projection data, the reconstruction method comprising the steps of:
  (a) collecting the projection data generated by the imaging system;
  (b) choosing a polar or cylindrical image definition which comprises a polar or cylindrical grid representation and a number of basis functions positioned according to the polar or cylindrical grid so that the number of basis functions at different radius positions of the polar or cylindrical image grid is a factor of a number of in-plane symmetries between lines of response along which the projection data are measured by the imaging system;
  (c) obtaining a system probability matrix that relates each of the projection data to each basis function of the polar image definition;
  (d) restructuring the system probability matrix into a block circulant matrix and converting the system probability matrix in Fourier domain to accelerate matrix-vector operations using the system probability matrix;
  (e) storing and arranging in a suitable form the projection data into a measurement data vector;
  (f) providing an initial polar or cylindrical image estimate;
  (g) for each iteration and using an iterative solver;
    (i) converting the polar or cylindrical image estimate in the Fourier domain so that it can be forward projected with the system probability matrix in the Fourier domain to obtain a measurement data estimate that is further converted back in space domain using the inverse Fourier transform;
    (ii) computing a measurement correction vector using the measurement data estimate and the measurement data vector;
    (iii) converting the measurement correction vector in the Fourier domain so that it can be back projected with the system probability matrix in the Fourier domain to obtain a polar or cylindrical image correction vector that is further converted back in the space domain using the inverse Fourier transform; and
    (iv) computing a new polar or cylindrical image estimate using a current polar or cylindrical image estimate and the polar or cylindrical image correction vector; going back to step (i) for further iterations until the polar or cylindrical image estimate reaches convergence; and
  (h) converting the polar or cylindrical image estimate into a Cartesian image representation to thereby obtain a reconstructed image.

15. A method as recited in claim 14, wherein collecting the projection data generated by the imaging system comprises collecting the projection data along a two-dimensional slice of a given object and wherein the polar image is a two-dimensional image.

16. A method as recited in claim 15, wherein the basis functions have a shape selected from the group consisting of a pie shape, a truncated pie shape, a circle, a blob, a square and a rectangle.

17. A method as recited in claim 14, wherein collecting the projection data generated by the imaging system comprises collecting the projection data along a three-dimensional volume of a given object and wherein the cylindrical image is a three-dimensional image.

18. A method as recited in claim 17, wherein the basis functions have a shape selected from the group consisting of a pie shape volume, a truncated pie shape volume, a cylindrical volume, a sphere, a blob, a cube and a rectangular volume.

19. A method as recited in claim 14, further comprising storing the system probability matrix in the Fourier domain in a sparse matrix format.

20. A method as recited in claim 14, wherein restructuring the system probability matrix into the block circulant matrix comprises using the in-plane symmetries to restructure the probability matrix as the block circulant matrix, which is formed by a plurality of block circulant matrices.

21. A method as recited in claim 20, wherein restructuring the system probability matrix into the block circulant matrix comprising using axial symmetries of the imaging system to restructure the probability matrix as the block circulant matrix, which is formed by a plurality of block circulant matrices.

22. A method as recited in claim 21, further comprising performing Fourier Transforms twice on the system probability matrix a first time according to the block circulant structure provided by the in-plane symmetries and a second time according to the block circulant structure provided by the axial symmetries.

23. A method as recited in claim 21, wherein using the axial symmetries simplifies reconstruction of a three-dimensional image.

24. A method as recited in claim 14, wherein the iterative solver is a Maximum Likelihood Expectation Maximization (MLEM) algorithm.

25. A method as recited in claim 14, wherein the iterative solver is an Ordered Subset Expectation Maximization (OSEM) algorithm.

26. A method as recited in claim 14, wherein the iterative solver is a block iterative image reconstruction method.

27. A method as recited in claim 14, wherein the forward and backward projection operations in step (g) are only applied to a subset of the polar or cylindrical image estimates.

28. A method as recited in claim 14, wherein the forward and backward projection operations in step (g) are only applied to a subset of the measurement correction vectors.

29. A method as recited in claim 14, wherein choosing the polar or cylindrical image definition comprises choosing a polar or cylindrical image having a polar or cylindrical grid definition such that a larger amount of the basis functions are defined for outermost radius positions of the polar or cylindrical grid than for innermost radius positions.

30. A method as recited in claim 14, wherein computing the new polar or cylindrical image estimate in step (g) (iv), further comprises combining a plurality of pixels values of the polar or cylindrical image estimate and of the polar or cylindrical image correction vector before computing the new polar or cylindrical image estimate.

31. A method as recited in claim 14, wherein computing the new polar or cylindrical image estimate in step (g) (iv), further comprises combining a plurality of voxels values of the polar or cylindrical image estimate and of the polar or cylindrical image correction vector before computing the new polar or cylindrical image estimate.

32. A method as recited in claim 14, wherein computing the new polar or cylindrical image estimate in step (g) (iv), further comprises transforming the polar or cylindrical image estimate and the polar or cylindrical image correction vector into Cartesian image representations in order to compute the new image estimate using the Cartesian image representations; the new image estimate being then reconverted into the polar or cylindrical image representation to carry on iterations.

33. A method as recited in claim 14, wherein obtaining the system probability matrix comprises using analytical methods for obtaining coefficients of the probability matrix.

34. A method as recited in claim 33, wherein obtaining the system probability matrix comprises using Monte Carlo simulations for obtaining the coefficients of the system probability matrix.

35. A method as recited in claim 34, wherein obtaining the system probability matrix further comprises using a method that models the lines of response of the imaging system by an infinite thin line, by a strip or by a tube.

36. A method as recited in claim 14, further comprising using an equivalence of Fourier transform operations to accelerate matrix-vector operations between the block circulant matrix and the measurement correction vector and the polar or cylindrical image estimate.

37. A method as recited in claim 21, further comprising a method to extend a number of the axial symmetries of the imaging system, which comprises the step of:
(a) collecting different projection data frames taken at different axial bed positions;
(b) recombining the different projection data frames in order to increase statistics of the collected projection data frames at the different axial bed positions so as to obtain a new extended projection data set;
(c) computing a system probability matrix for this new extended projection data set, which relates each of the projection data to each basis function of the polar image definition; and
(d) reconstructing an image using the system probability matrix and the extended projection data set.

38. A method as recited in claim 14, further comprising using approximations on a geometry of the imaging system in order to increase a number of in-plane and axial symmetries.

39. A method as recited in claim 14, wherein the polar or cylindrical image has different numbers of pixels at different radius positions.

40. A direct image reconstruction method to be used in connection with an imaging system that generates projection data, the method comprising the steps of:
(a) collecting the projection data generated by the imaging system;
(b) choosing a polar or cylindrical image definition which comprises a polar or cylindrical grid representation and a number of basis functions positioned according to the polar or cylindrical grid so that the number of basis functions at different radius positions of the polar or cylindrical image grid is a factor of a number of in-plane symmetries between lines of response along which the projection data are measured by the imaging system;
(c) computing a system probability matrix that relates each of the projection data to each basis function of the polar or cylindrical grid representation;
(d) restructuring the system probability matrix into a block circulant matrix and converting the system probability matrix in Fourier domain to accelerate matrix-vector operations when using the system probability matrix;
(e) storing and arranging in a suitable form the projection data into a measurement data vector;
(f) pseudo-inverting the block circulant matrix using singular value decomposition (SVD) to produce a pseudo-inverse of the circulant matrix;
(g) computing a polar or cylindrical image estimate by performing a matrix-vector product in the Fourier domain between the pseudo-inverse of the circulant matrix and the measurement data vector; and
(k) converting the polar or cylindrical image estimate into a Cartesian image representation to thereby obtain a reconstructed image.

41. A method as recited in claim 40, wherein the pseudo-inversion operation of the block circulant system matrix is performed each time that a new projection data is collected.

42. A method as recited in claim 40, wherein the pseudo-inversion operation of the block circulant system matrix is performed only once in a pre-computation step and results of the SVD are used to reconstruct the image.

43. A method as recited in claim 40, wherein the pseudo-inversion operation of the block circulant system matrix is performed only once in a pre-computation step to produce the pseudo-inverted matrix.

44. A method as recited in claim 43, wherein the pseudo-inverted system matrix is regularized by using troncated singular values.

45. A method as recited in claim 43, wherein the pseudo-inverted system matrix is regularized by using weighted singular values.

46. A method as recited in claim 44, wherein different regularization operations are performed for pixels at different positions in the image.

47. A method as recited in claim 40, wherein restructuring the system probability matrix into the block circulant matrix comprises using in-plane symmetries of the imaging system.

48. A method as recited in claim 47, wherein restructuring the system probability matrix into the block circulant matrix comprises using axial symmetries of the imaging system.

49. A method as recited in claim 48, wherein the block circulant matrix comprises a plurality of block circulant matrices.

50. A method as recited in claim 48, further comprising performing Fourier transforms twice on the system probability matrix, a first time according to the block circulant structure given by the in-plane symmetries and a second time according to the block circulant structure given by the axial symmetries.

51. A method as recited in claim 40, wherein the factor of the number of the in-plane symmetries between the lines of response is an element selected from the group consisting of equal to, an integer fraction of and an integer multiple of.

* * * * *